United States Patent
Marappan et al.

(10) Patent No.: US 7,250,412 B2
(45) Date of Patent: Jul. 31, 2007

(54) PH SENSITIVE PRODRUGS OF 2,6-DIISOPROPYLPHENOL

(75) Inventors: Subramanian Marappan, San Diego, CA (US); Cris Davenport, Placentia, CA (US); Sepehr Sarshar, Cardiff by the Sea, CA (US)

(73) Assignee: Auspex Pharmaceuticals, Inc., Vista, CA (US)

( * ) Notice: Subject to any disclaimer, the term of this patent is extended or adjusted under 35 U.S.C. 154(b) by 221 days.

(21) Appl. No.: 10/514,303

(22) PCT Filed: Mar. 15, 2004

(86) PCT No.: PCT/US2004/007935

§ 371 (c)(1),
(2), (4) Date: Jun. 17, 2005

(87) PCT Pub. No.: WO2005/044201

PCT Pub. Date: May 19, 2005

(65) Prior Publication Data

US 2005/0234050 A1    Oct. 20, 2005

(51) Int. Cl.
| | |
|---|---|
| A61K 31/54 | (2006.01) |
| A61K 31/165 | (2006.01) |
| A61K 31/40 | (2006.01) |
| A61K 31/415 | (2006.01) |
| A61K 31/4164 | (2006.01) |
| A61K 31/4192 | (2006.01) |
| A61K 31/4196 | (2006.01) |
| A61K 31/426 | (2006.01) |
| A61K 31/4453 | (2006.01) |
| A61K 31/505 | (2006.01) |
| A61K 31/495 | (2006.01) |
| A61K 31/53 | (2006.01) |
| A61K 31/5375 | (2006.01) |

(52) U.S. Cl. ............... 514/227.5; 514/428; 514/237.8; 514/241; 514/252.12; 514/252.1; 514/256; 514/331; 514/357; 514/365; 514/374; 514/383; 514/399; 514/406; 514/427; 548/235; 548/255; 548/204; 548/267.2

(58) Field of Classification Search .......... 514/227.5, 514/237.8, 241, 252.12, 252.1, 256, 331, 514/357, 365, 374, 383, 399, 406, 427, 428; 544/59, 106, 180, 335, 400; 546/229, 336; 548/235, 255, 204, 267, 568, 338.1, 375.1
See application file for complete search history.

(56) References Cited

U.S. PATENT DOCUMENTS

| | | | |
|---|---|---|---|
| 6,204,257 B1 | 3/2001 | Stella et al. |
| 6,254,853 B1 | 7/2001 | Hendler et al. |
| 6,362,234 B1 | 3/2002 | Hendler et al. |
| 6,872,838 B2 | 3/2005 | Stella et al. |

FOREIGN PATENT DOCUMENTS

| | | |
|---|---|---|
| JP | 2002-275065 | 9/2002 |
| WO | WO 9115464 A1 * | 10/1991 |

OTHER PUBLICATIONS

Banaszczyk et al., "Propofol Phosphate, a Water-Soluble Propofol Prodrug: In Vivo Evaluation," Anesth. Analog, 2002, vol. 95, pp. 1285-92.
Sliskovic et al., "Inhibitors of Acyl-CoA: Cholesterol 0-Acyl Transferase (ACAT) as Hypocholesterolemic Agents. The Synthesis and Biological Activity of a Series of Malonester Amides," Bioorganic & Medicinal Chemistry Letters, 1996, 6:6, pp. 713-718.
Bennett et al., "Novel Water Soluble 2,6-Dimethoxyphenyl Ester Derivatives with Intravenous Anaesthetic Activity," Bioorganic & Medicinal Chemistry Letters, vol. 13, 2003, pp. 1971-1975.
Trapani et al., "Water-soluble salts of aminoacid esters of the anaesthetic agent Propofol", International Journal of Pharmaceutics, vol. 175, 1998, pp. 195-204.
Sohma et al., "Development of Water-Soluble Prodrugs of the HIV-1 Protease Inhibitor KNI-727: Importance of the Conversion Time for Higher Gastrointestinal Absorption of Prodrugs Based on Spontaneous Chemical Cleavage," J. Med. Chem., 2003, vol. 46, pp. 4124-4135.
Fechner et al., "Pharmacokinetics and Clinical Pharmacodynamics of the New Propofol Prodrug GPI 15715 in Volunteers," Anesthesiology, 2003, vol. 99, pp. 303-313.
Lee et al., "Inhibitors of ACYL-CoA: Cholesterol O-Acyltransferase (ACAT) as Hypocholesterolemic Agents: Synthesis and Structure-Activity Relationships of Novel Series of Sulfonamides, Acylphosphonamides and Acylphosphoramidates," Bioorganic and Medicinal Chemistry Letters, vol. 8, 1998, pp. 289-294.
Altomare et al., "Highly water-soluble derivatives of the anesthetic agent propofol: in vitro and in vivo evaluation of cyclic amino acid esters," European Journal of Pharmceutical Sciences, vol. 20, 2003, pp. 17-26.
Trapani et al., "Propofol Analogues. Synthesis, Relationshis between Structure and Affinity at GABAA Receptor in Rat Brain, and Differential Electrophysiological Profile at Recombinant Human GABAA Receptors", J. Med. Chem 1998, vol. 41, 1846-1854.

(Continued)

Primary Examiner—Kamal A. Saeed
Assistant Examiner—Michael P. Barker
(74) Attorney, Agent, or Firm—DLA Piper US LLP

(57) ABSTRACT

The present invention is directed to water-soluble derivatives of 2,6-diisopropylphenol (Propofol). The compounds act as prodrugs of 2,6-diisopropylphenol and metabolize rapidly to Propofol thereby providing an alternative to the water-insoluble 2,6-diisopropylphenol. Pharmaceutical compositions comprising these compounds, methods of induction and maintenance of anesthesia or sedation as well as methods of treating neurodegenerative diseases utilizing pharmaceutical compositions comprising these compounds and methods of preparing them are also disclosed.

9 Claims, No Drawings

OTHER PUBLICATIONS

Lee et al., "Phenolic Modification as an Approach to Improve the Pharmacology of the 3-Acyloxy-2-benzylpropyl Homovanillic Amides and Thioureas, a Promising Class of Vanilloid Receptor Agonists and Alagesics", Bioorg. & Medic. Chem., vol. 10, 2002, pp. 1171-1179.

Cooke et al., "Water-Soluble Propofol Analogues with Intravenous Anaesthetic Activity", Bioorganic and Medicinal Chemistry Letters, vol. 11, 2001, pp. 927-930.

Trapani et al., "Effect of 2-hydroxypropyl-beta-cyclodextrin on the aqueous solubility of the anaesthetic agent propofol (2,6-diisopropylphenol)", International Journal of Pharmaceutics, vol. 139, 1996, pp. 215-218.

Anderson et al., "alpha-amino Acid Phenolic Ester Derivatives: Novel Water-Soluble General Anesthetic Agents Which Allosterically Modulate GABAA Receptors", J. Med. Chem, 2001, vol. 44, pp. 3582-3591.

* cited by examiner

PH SENSITIVE PRODRUGS OF 2,6-DIISOPROPYLPHENOL

FIELD OF THE INVENTION

The invention relates generally to prodrugs and more specifically to water-soluble derivatives of 2,6-diisopropylphenol (Propofol).

BACKGROUND OF THE INVENTION 2,6-diisopropylphenol is highly lipophilic and is practically insoluble in water. For intravenous applications, it is formulated in water using a variety of solubilizing agents and/or emulsifiers. Examples of such formulations include Cremophor™, Intralipid™, Diprivan™, Disoprofol™, Disoprivan™, and Rapinovet™. The aforementioned formulations have many limitations. They cause allergic side effects and pain upon injection. Their preparation is difficult and costly and most importantly they cannot be sterilized and hence anti-microbial agents must be added to the formulations.

Propofol or 2,6-diisopropylphenol is a short acting anesthetic that is administered intravenously (i.v.) to mammalian subjects. The low water solubility of this compound presents a significant formulation challenge. The currently approved mode of administration for Propofol is an emulsion that has many disadvantages including costly preparation and sterilization procedures. Oxidation of Propofol to unwanted side-products in the presence of oxygen and light drastically shortens the shelf life of such formulations. In addition, the oil-in-water emulsions cause a number of clinical side effects including pain on injection and pulmonary embolism.

Thus, there exists a clear need for a water-soluble, stable, non-toxic pharmaceutical composition of 2,6-diisopropylphenol.

SUMMARY OF THE INVENTION

The present invention describes non-toxic and water-soluble derivatives of 2,6-diisopropylphenol or Propofol, a low molecular weight alcohol that is administered intravenously and serves as a sedative-hypnotic agent in humans and animals. 2,6-diisopropylphenol has a broad range of applications. It is an antioxidant and inhibits lipid peroxidation. It can also act as an anti-inflammatory agent and can useful in the treatment of acid aspiration, respiratory distress syndrome, airway obstructive disease, asthma, bronchiolitis, bronchopulmonary dysplasia, cancer, chronic obstructive pulmonary disease ("COPD"), cystic fibrosis, emphysema, HIV-associated lung disease, idiopathic pulmonary fibrosis, immune-complex-mediated lung injury, exposure to an oxidizing agent, ischemia-reperfusion injury, mineral dust pneumoconiosis, drug-induced lung disease, silo-filler's disease, and various neurodegenerative diseases such as Friedrich's disease, Parkinson's disease, Alzheimer's disease, Huntington's disease, amyotrophic lateral sclerosis (ALS); multiple sclerosis (MS), Pick disease, spinal cord injury, acute neural injury and aging.

The present invention is directed to water-soluble derivatives of 2,6-diisopropylphenol. The compounds of the invention act as pH sensitive prodrugs of 2,6-diisopropylphenol that degrade and metabolize rapidly to Propofol upon intravenous injection. The compounds of this invention are crystalline solids that are stable at or below ambient temperature and can be stored as aqueous solutions if the pH of the solution is kept in the range of 0 to 6. Such characteristics represent clear economic and clinical improvements over the state of the art.

In one aspect, this invention describes 2,6-diisopropylphenol derivatives according to formula A:

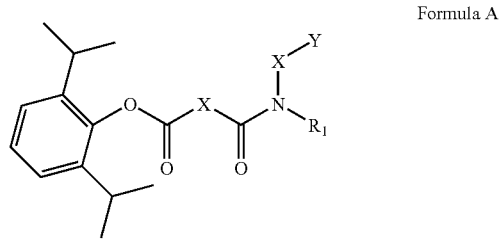

Formula A wherein:

$R_1$ is hydrogen, alkyl, or aryl;

Each X is independently $C_{1-10}$ alkyl;

Y is heteroaryl, saturated heterocyclic, or $NR_2R_3$, $R_2$ and $R_3$ are independently hydrogen, alkyl, or $R_2$ and $R_3$, together with the nitrogen atom to which they are attached, combine to form a saturated heterocyclic or heteroaryl ring;

or a pharmaceutically acceptable salt of any of the foregoing.

Specifically, the compounds of the present invention convert to 2,6-diisopropylphenol in vivo and can be used as hypnotic agents, anti-convulsives, anti-pruritics, and anti-emetics. Other uses include treatment of oxidative tissue damage, inflammation and cancer. The prodrug compounds of the present invention have many advantages over 2,6-diisopropylphenol by virtue of increased aqueous solubility and increased stability towards oxidation over the parent compound thus making them particularly suitable for intravenous (i.v.) formulations. Therefore when used in a mammalian subject, the compounds of this invention replicate every therapeutic application that has been described for 2,6-diisopropylphenol. Other advantages of the compounds of the present invention include low toxicity and high therapeutic-to-toxicity index.

In another aspect, this invention is directed to a pharmaceutical composition comprising one or more compound (s) of Formula A, or a pharmaceutically acceptable salt thereof and a pharmaceutically acceptable excipient.

In another aspect, this invention provides a method for inhibiting oxidation of biological material comprising contacting the material with an effective amount of a pharmaceutical composition comprising one or more compound (s) of Formula A, or a pharmaceutically acceptable salt thereof and a pharmaceutically acceptable excipient.

In another aspect, this invention provides a method for the treatment of a pathologic condition having an inflammatory component in a subject comprising administering to the subject a pharmaceutical composition comprising one or more compound (s) of Formula A, or a pharmaceutically acceptable salt thereof and a pharmaceutically acceptable excipient.

In another aspect, this invention provides a method for the treatment of a pathologic condition of the nervous system having an inflammatory component in a subject comprising administering to the subject a pharmaceutical composition comprising one or more compound (s) of Formula A, or a pharmaceutically acceptable salt thereof and a pharmaceutically acceptable excipient.

In another aspect, this invention provides a method for the treatment of a pathologic respiratory condition in a subject comprising administering to the subject a pharmaceutical composition comprising one or more compound (s) of Formula A, or a pharmaceutically acceptable salt thereof and a pharmaceutically acceptable excipient.

In another aspect, this invention provides a method for inducing anesthesia in a subject comprising administering to the subject a pharmaceutical composition comprising one or more compound (s) of Formula A, or a pharmaceutically acceptable salt thereof and a pharmaceutically acceptable excipient.

In another aspect, this invention provides a method for inhibiting nausea and vomiting in a subject comprising administering to the subject a pharmaceutical composition comprising one or more compound (s) of Formula A, or a pharmaceutically acceptable salt thereof and a pharmaceutically acceptable excipient.

In another aspect, this invention provides a method for the treatment of epileptic or convulsive disorders in a subject comprising administering to the subject a pharmaceutical composition comprising one or more compound (s) of Formula A, or a pharmaceutically acceptable salt thereof and a pharmaceutically acceptable excipient.

In another aspect, this invention provides a method for the treatment of pruritis in a subject comprising administering to the subject a pharmaceutical composition comprising one or more compound (s) of Formula A, or a pharmaceutically acceptable salt thereof and a pharmaceutically acceptable excipient.

In another aspect, this invention provides pharmaceutical compositions comprising at least one of the compounds of the invention, in a pharmaceutically acceptable vehicle, for the treatment of carcinomas. Examples of carcinomas include mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia, and the like.

In another aspect, this invention provides pharmaceutical compositions comprising at least one the compounds of the invention in combination with other chemotherapeutic agents, in a pharmaceutically acceptable vehicle, for the treatment of carcinomas. Examples of chemotherapeutic agents contemplated for use in the practice of this particular invention include Busulfan, Carboplatin, Cisplatin, Cyclophosphamide, Cytosine arabinoside, Etoposide, 5-Fluorouracil, Melphalan, Methotrexate, Mitoxantrone, Taxol, Interferon, Fareston, Arzoxifene, Evista, Tamoxifen, and the like.

In another aspect, this invention provides a method for the treatment of a subject undergoing treatment with a chemotherapeutic agent having activity as an oxidizing agent comprising the step of administering a pharmaceutical composition comprising one or more compound (s) of Formula A, or a pharmaceutically acceptable salt thereof and a pharmaceutically acceptable excipient.

In another aspect, this invention provides a method for the use of compounds of Formula A in the manufacture of a medicament for the treatment of a pathological condition having an inflammatory component.

The non-limiting examples shown in schemes 1-3, illustrate the inventors' preferred methods for carrying out the preparative process of the invention.

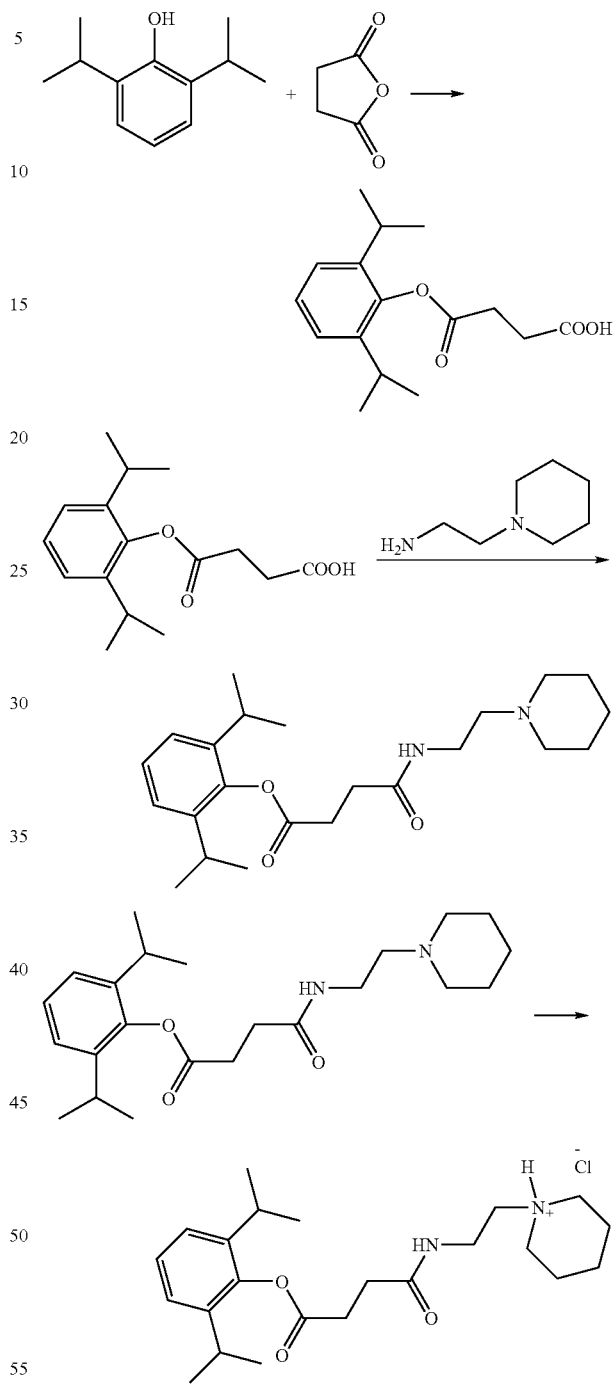

Scheme 1

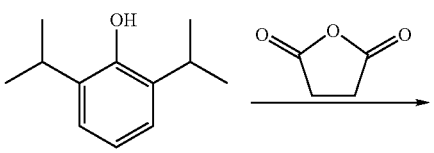

Scheme 2

-continued

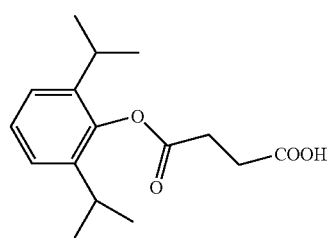

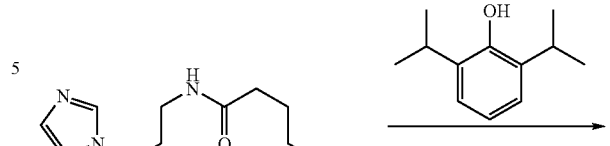

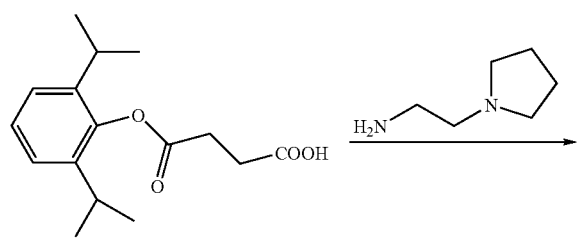

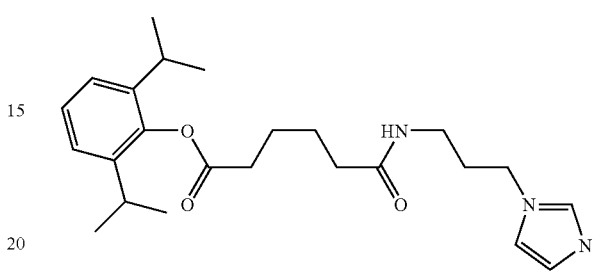

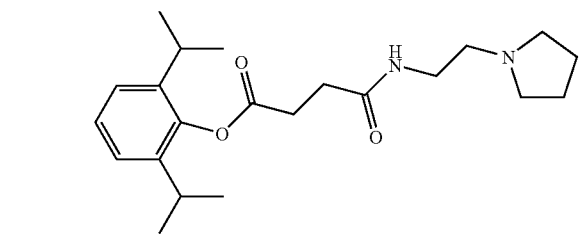

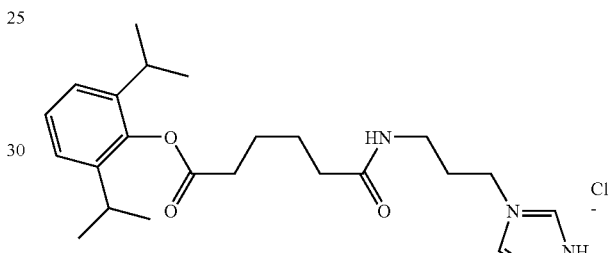

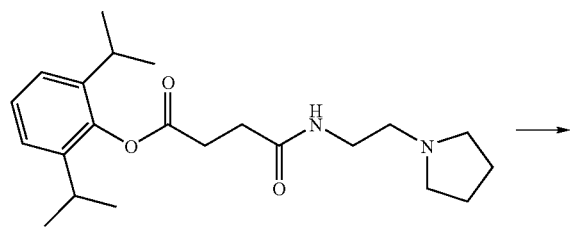

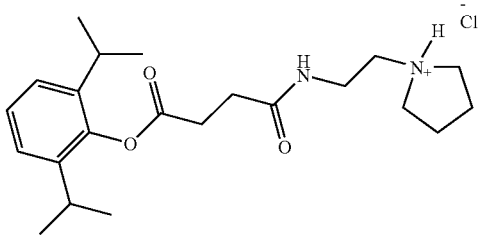

Scheme 3

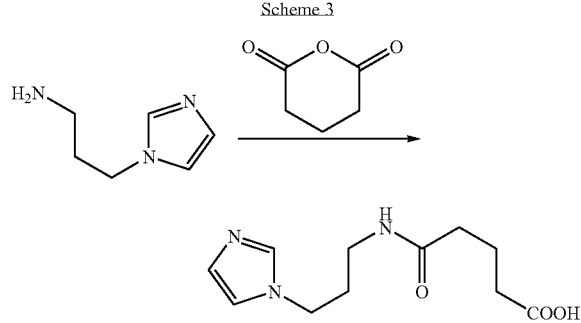

DETAILED DESCRIPTION OF THE INVENTION

In one aspect of the invention, there are provided compounds comprising the structural formula A:

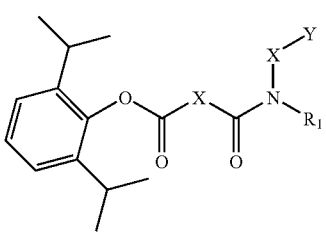

Formula A wherein:
R$_1$ is hydrogen, alkyl, or aryl;
Each X is independently C$_{1-10}$ alkyl;
Y is heteroaryl, saturated heterocyclic, or NR$_2$R$_3$,
R$_2$ and R$_3$ are independently hydrogen, alkyl, or R$_2$ and R$_3$, together with the nitrogen atom to which they are attached, combine to form a saturated heterocyclic or heteroaryl ring; or a pharmaceutically acceptable salt of any of the foregoing.

The compounds according to this invention may contain one or more asymmetric carbon atoms and can thus occur as racemates and racemic mixtures, single enantiomers, diastereomeric mixtures or individual diastereomers. The term "stereoisomer" refers to a chemical compound having the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. The compounds described herein may have one or more asymmetrical carbon atoms and therefore include various stereoisomers. All such isomeric forms of these compounds are expressly included in the present invention.

Each stereogenic carbon may be of R or S configuration. Although the specific compounds exemplified in this application may be depicted in a particular configuration, compounds having either the opposite stereochemistry at any given chiral center or mixtures thereof are also envisioned. When chiral centers are found in the derivatives of this invention, it is to be understood that this invention encompasses all possible stereoisomers.

The terms "optically pure compound" or "optically pure isomer" refers to a single stereoisomer of a chiral compound regardless of the configuration of the said compound.

For purpose of this application, all sugars are referenced using conventional three-letter nomenclature. All sugars are assumed to be in the D-form unless otherwise noted, except for fucose, which is in the L-form. Further, all sugars are in the pyranose form.

The compounds according to this invention may occur as a mixture of tautomers. The term "tautomer" or "tautomerism" refer to one of two or more structural isomers that exist in equilibrium and are readily converted from one isomeric form to another. Examples of include keto-enol tautomers, such as acetone/propen-2-ol and the like, ring-chain tautomers, such as glucose/2,3,4,5,6-pentahydroxy-hexanal and the like. The compounds described herein may have one or more tautomers and therefore include various isomers. All such isomeric forms of these compounds are expressly included in the present invention. The following example of tautomerism is provided for reference:

N-(2-Pyrrolidin-1-yl-ethyl)-succinamic acid 2,6-diisopropyl-phenyl ester

The term "substantially homogeneous" refers to collections of molecules wherein at least 80%, preferably at least about 90% and more preferably at least about 95% of the molecules are a single compound or a single stereoisomer thereof.

As used herein, the term "attached" signifies a stable covalent bond, certain preferred points of attachment being apparent to those skilled in the art.

The terms "optional" or "optionally" refer to occurrence or non-occurrence of the subsequently described event or circumstance, and that the description includes instances where said event or circumstance occurs and instances where it does not. In such context, the sentence "optionally substituted alkyl group" means that the alkyl group may or may not be substituted and the description includes both a substituted and an unsubstituted alkyl group.

The term "effective amount" of a compound refers a non-toxic but sufficient amount of the compound that provides a desired effect. This amount may vary from subject to subject, depending on the species, age, and physical condition of the subject, the severity of the disease that is being treated, the particular compound used, its mode of administration, and the like. Therefore, it is difficult to generalize an exact "effective amount", yet, a suitable effective amount may be determined by one of ordinary skill in the art.

The term "pharmaceutically acceptable" refers to a compound, additive or composition that is not biologically or otherwise undesirable. For example, the additive or composition may be administered to a subject along with a compound of the invention without causing any undesirable biological effects or interacting in an undesirable manner with any of the other components of the pharmaceutical composition in which it is contained.

The term "pharmaceutically acceptable salts" includes hydrochloric salt, hydrobromic salt, hydroiodic salt, hydrofluoric salt, sulfuric salt, citric salt, maleic salt, acetic salt, lactic salt, nicotinic salt, succinic salt, oxalic salt, phosphoric

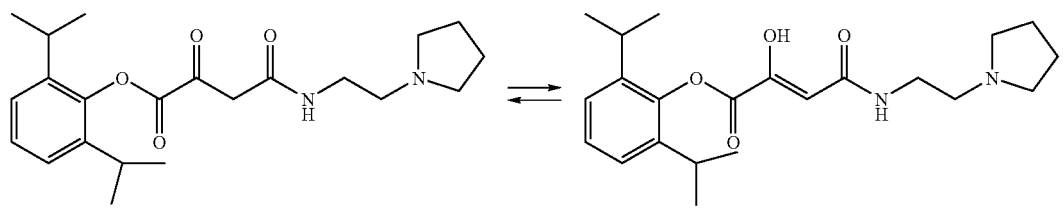

The following example of nomenclature and numbering system is provided for reference.

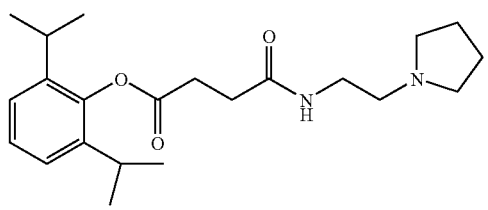

salt, malonic salt, salicylic salt, phenylacetic salt, stearic salt, pyridine salt, ammonium salt, piperazine salt, diethylamine salt, nicotinamide salt, formic salt, urea salt, sodium salt, potassium salt, calcium salt, magnesium salt, zinc salt, lithium salt, cinnamic salt, methylamino salt, methanesulfonic salt, picric salt, tartaric salt, triethylamino salt, dimethylamino salt, tris (hydroxymethyl)aminomethane salt and the like. Additional pharmaceutically acceptable salts are known to those of skill in the art.

When used in conjunction with a compound of this invention, the terms "elicite", "eliciting," "modulator", "modulate", "modulating", "regulator", "regulate" or "regulating" selective gene expression refer to a compound that can act as an activator, an agonist, a pan-agonist or an antagonist of gene expression by a particular receptor, such as for example a Retinoid X Receptor and the like.

The terms "therapeutic agent" and "chemotherapeutic agent", refer to a compound or compounds and pharmaceutically acceptable compositions thereof that are administered to mammalian subjects as prophylactic or remedy in the treatment of a disease or medical condition. Such compounds may be administered to the subject via oral formulation, transdermal formulation or by injection.

The term "Lewis acid" refers to a molecule that can accept an unshared pair of electrons and as such would be obvious to one of ordinary skill and knowledge in the art. The definition of "Lewis acid" includes but is not limited to: boron trifluoride, boron trifluoride etherate, boron trifluoride tetrahydrofuran complex, boron trifluoride tert-butyl-methyl ether complex, boron trifluoride dibutyl ether complex, boron trifluoride dihydrate, boron trifluoride di-acetic acid complex, boron trifluoride dimethyl sulfide complex, boron trichloride, boron trichloride dimethyl sulfide complex, boron tribromide, boron tribromide dimethyl sulfide complex, boron triiodide, triimethoxyborane, triethoxyborane, trimethylaluminum, triethylaluminum, aluminum trichloride, aluminum trichloride tetrahydrofuran complex, aluminum tribromide, titanium tetrachloride, titanium tetrabromide, titanium iodide, titanium tetraethoxide, titanium tetraisopropoxide, scandium (III) trifluoromethanesulfonate, yttrium (III) trifluoromethanesulfonate, ytterbium (III) trifluoromethanesulfonate, lanthanum (III) trifluoromethanesulfonate, zinc (II) chloride, zinc (II) bromide, zinc (II) iodide, zinc (II) trifluoromethanesulfonate, zinc (II) sulfate, magnesium sulfate, lithium perchlorate, copper (II) trifluoromethanesulfonate, copper (II) tetrafluoroborate and the like. Certain Lewis acids may have optically pure ligands attached to the electron acceptor atom, as set forth in Corey, E. J. Angewandte Chemie, International Edition (2002), 41 (10), 1650-1667; Aspinall, H. C. Chemical Reviews (Washington, D.C., United States) (2002), 102 (6), 1807-1850; Groger, H. Chemistry—A European Journal (2001), 7 (24), 5246-5251; Davies, H. M. L. Chemtracts (2001), 14 (11), 642-645; Wan, Y. Chemtracts (2001), 14 (11), 610-615; Kim, Y. H. Accounts of Chemical Research (2001), 34 (12), 955-962; Seebach, D. Angewandte Chemie, International Edition (2001), 40 (1), 92-138; Blaser, H. U. Applied Catalysis, A: General (2001), 221 (1-2), 119-143; Yet, L. Angewandte Chemie, International Edition (2001), 40 (5), 875-877; Jorgensen, K. A. Angewandte Chemie, International Edition (2000), 39 (20), 3558-3588; Dias, L. C. Current Organic Chemistry (2000), 4 (3), 305-342; Spindler, F. Enantiomer (1999), 4 (6), 557-568; Fodor, K. Enantiomer (1999), 4 (6), 497-511; Shimizu, K. D.; Comprehensive Asymmetric Catalysis I-III (1999), 3,1389-1399; Kagan, H. B. Comprehensive Asymmetric Catalysis I-III (1999), 1, 9-30; Mikami, K. Lewis Acid Reagents (1999), 93-136 and all references cited therein. Such Lewis acids maybe used by one of ordinary skill and knowledge in the art to produce optically pure compounds from achiral starting materials.

The term "acylating agent" refers to a molecule that can transfer an alkylcarbonyl, substituted alkylcarbonyl or aryl carbonyl group to another molecule. The definition of "acylating agent" includes but is not limited to ethyl acetate, vinyl acetate, vinyl propionate, vinyl butyrate, isopropenyl acetate, 1-ethoxyvinyl acetate, trichloroethyl butyrate, trifluoroethyl butyrate, trifluoroethyl laureate, S-ethyl thiooctanoate, biacetyl monooxime acetate, acetic anhydride, acetyl chloride, succinic anhydride, diketene, diallyl carbonate, carbonic acid but-3-enyl ester cyanomethyl ester, amino acid and the like.

The term "nucleophile" or "nucleophilic reagent" refers to a negatively charged or neutral molecule that has an unshared pair of electrons and as such would be obvious to one of ordinary skill and knowledge in the art. The definition of "nucleophile" includes but is not limited to: water, alkylhydroxy, alkoxy anion, arylhydroxy, aryloxy anion, alkylthiol, alkylthio anion, arylthiol, arylthio anion, ammonia, alkylamine, arylamine, alkylamine anion, arylamine anion, hydrazine, alkyl hydrazine, arylhydrazine, alkylcarbonyl hydrazine, arylcarbonyl hydrazine, hydrazine anion, alkyl hydrazine anion, arylhydrazine anion, alkylcarbonyl hydrazine anion, arylcarbonyl hydrazine anion, cyanide, azide, hydride, alkyl anion, aryl anion and the like.

The term "electrophile" or "electrophilic reagent" refers to a positively charged or neutral molecule that has an open valence shell and as such would be obvious to one of ordinary skill and knowledge in the art. The definition of "electrophile" includes but is not limited to: hydronium, acylium, lewis acids, such as for example, boron trifluoride and the like, halogens, such as for example $Br_2$ and the like, carbocations, such as for example tert-butyl cation and the like, diazomethane, trimethylsilyldiazomethane, alkyl halides, such as for example methyl iodide, benzyl bromide and the like, alkyl triflates, such as for example methyl triflate and the like, alkyl sulfonates, such as for example ethyl toluenesulfonate, butyl methanesulfonate and the like, acyl halides, such as for example acetyl chloride, benzoyl bromide and the like, acid anhydrides, such as for example acetic anhydride, succinic anhydride, maleic anhydride and the like, isocyanates, such as for example methyl isocyanate, phenylisocyanate and the like, chloroformates, such as for example methyl chloroformate, ethyl chloroformate, benzyl chloroformate and the like, sulfonyl halides, such as for example methanesulfonyl chloride, p-tolunesulfonyl chloride and the like, silyl halides, such as for example trimethylsilyl chloride, tertbutyldimethyl silyll chloride and the like, phosphoryl halide such as for example dimethyl chlorophosphate and the like, alpha-beta-unsaturated carbonyl compounds such as for example acrolein, methyl vinyl ketone, cinnamaldehyde and the like.

The term "leaving group" refers to any atom (or group of atoms) that is stable in its anion or neutral form after it has been displaced by a nucleophile and as such would be obvious to one of ordinary skill and knowledge in the art. The definition of "leaving group" includes but is not limited to: water, methanol, ethanol, chloride, bromide, iodide, methanesulfonate, tolylsulfonate, trifluoromethanesulfonate, acetate, trichloroacetate, benzoate and the like.

The term "oxidant" refers to any reagent that will increase the oxidation state of a carbon atom in the starting material by either adding an oxygen atom to this carbon or removing an electron from this carbon and as such would be obvious to one of ordinary skill and knowledge in the art. The definition of "oxidant" includes but is not limited to: osmium tetroxide, ruthenium tetroxide, ruthenium trichloride, potassium permanganate, meta-chloroperbenzoic acid, hydrogen peroxide, dimethyl dioxirane and the like.

The term "metal ligand" refers to a molecule that has an unshared pair of electrons and can coordinate to a metal atom and as such would be obvious to one of ordinary skill and knowledge in the art. The definition of "metal ligand" includes but is not limited to: water, alkoxy anion, alkylthio anion, ammonia, trialkylamine, triarylamine, trialkylphosphine, triarylphosphine, cyanide, azide and the like.

The term "reducing reagent" refers to any reagent that will decrease the oxidation state of a carbon atom in the starting material by either adding a hydrogen atom to this carbon or adding an electron to this carbon and as such would be obvious to one of ordinary skill and knowledge in the art. The definition of "reducing reagent" includes but is not limited to: borane-dimethyl sulfide complex, 9-borabicyclo[3.3.1.]nonane (9-BBN), catechol borane, lithium borohydride, sodium borohydride, sodium borohydride-methanol complex, potassium borohydride, sodium hydroxyborohydride, lithium triethylborohydride, lithium n-butylborohydride, sodium cyanoborohydride, calcium (II) borohydride, lithium aluminum hydride, diisobutylaluminum hydride, n-butyl-diisobutylaluminum hydride, sodium bis-methoxyethoxyaluminum hydride, triethoxysilane, diethoxymethylsilane, lithium hydride, lithium, sodium, hydrogen Ni/B, and the like. Certain acidic and Lewis acidic reagents enhance the activity of reducing reagents. Examples of such acidic reagents include: acetic acid, methanesulfonic acid, hydrochloric acid, and the like. Examples of such Lewis acidic reagents include: trimethoxyborane, triethoxyborane, aluminum trichloride, lithium chloride, vanadium trichloride, dicyclopentadienyl titanium dichloride, cesium fluoride, potassium fluoride, zinc (II) chloride, zinc (II) bromide, zinc (II) iodide, and the like.

The term "coupling reagent" refers to any reagent that will activate the carbonyl of a carboxylic acid and facilitate the formation of an ester or amide bond. The definition of "coupling reagent" includes but is not limited to: acetyl chloride, ethyl chloroformate, dicyclohexylcarbodiimide (DCC), diisopropyl carbodiimide (DIC), 1-ethyl-3-(3-dimethylaminopropyl) carbodiimide (EDCl), N-hydroxybenzotriazole (HOBT), N-hydroxysuccinimide (HOSu), 4-nitrophenol, pentafluorophenol, 2-(1H-benzotriazole-1-yl)-1,1,3,3-tetramethyluronium tetrafluoroborate (TBTU), O-benzotriazole-N,N,N'N'-tetramethyluronium hexafluorophosphate (HBTU), benzotriazole-1-yl-oxy-tris-(dimethylamino)-phosphonium hexafluorophosphate (BOP), benzotriazole-1-yl-oxy-tris-pyrrolidinophosphonium hexafluorophosphate, bromo-trispyrrolidino-phosphonium hexafluorophosphate, 2-(5-norbornene-2,3-dicarboximido)-1,1,3,3-tetramethyluronium tetrafluoroborate (TNTU), O-(N-succinimidyl)-1,1,3,3-tetramethyluronium tetrafluoroborate (TSTU), tetramethylfluoroformamidinium hexafluorophosphate and the like.

The term "removable protecting group" or "protecting group" refers to any group which when bound to a functionality, such as the oxygen atom of a hydroxyl or carboxyl group or the nitrogen atom of an amino group, prevents reactions from occurring at these functional groups and which protecting group can be removed by conventional chemical or enzymatic steps to reestablish the functional group. The particular removable protecting group employed is not critical.

The definition of "hydroxyl protecting group" includes but is not limited to:

a) Methyl, tert-butyl, allyl, propargyl, p-chlorophenyl, p-methoxyphenyl, p-nitrophenyl, 2,4-dinitrophenyl, 2,3,5,6-tetrafluoro-4-(trifluoromethyl)phenyl, methoxymethyl, methylthiomethyl, (phenyldimethylsilyl)methoxymethyl, benzyloxymethyl, p-methoxy-benzyloxymethyl, p-nitrobenzyloxymethyl, o-nitrobenzyloxymethyl, (4-methoxyphenoxy)methyl, guaiacolmethyl, tert-butoxymethyl, 4-pentenyloxymethyl, tert-butyldimethylsiloxymethyl, thexyldimethylsiloxymethyl, tert-butyldiphenylsiloxymethyl, 2-methoxyethoxymethyl, 2,2,2-trichloroethoxymethyl, bis (2-chloroethoxy)methyl, 2-(trimethylsilyl)ethoxymethyl, menthoxymethyl, 1-ethoxyethyl, 1-(2-chloroethoxy)ethyl, 1-[2-(trimethylsilyl)ethoxy]ethyl, 1-methyl-1-ethoxyethyl, 1-methyl-1-benzyloxyethyl, 1-methyl-1-benzyloxy-2-fluoroethyl, 1-methyl-1-phenoxyethyl, 2,2,2-trichloroethyl, 1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydropyranyl S,S-dioxide, 1-[(2-chloro-4-methyl)phenyl]4-methoxypiperidin-4-yl, 1-(2-fluorophenyl)$_4$-methoxypiperidin-4-yl, 1,4-dioxan-2-yl, tetrahydrofuranyl, tetrahydrothiofuranyl and the like;

b) Benzyl, 2-nitrobenzyl, 2-trifluoromethylbenzyl, 4-methoxybenzyl, 4-nitrobenzyl, 4-chlorobenzyl, 4-bromobenzyl, 4-cyanobenzyl, 4-phenylbenzyl, 4acylaminobenzyl, 4-azidobenzyl, 4-(methylsulfinyl)benzyl, 2,4-dimethoxybenzyl, 4-azido-3-chlorobenzyl, 3,4-dimethoxybenzyl, 2,6-dichlorobenzyl, 2,6-difluorobenzyl, 1-pyrenylmethyl, diphenylmethyl, 4,4'-dinitrobenzhydryl, 5-benzosuberyl, triphenylmethyl(Trityl), α-naphthyldiphenylmethyl, (4-Methoxyphenyl)-diphenyl-methyl, di-(p-methoxyphenyl)-phenylmethyl, tri-(p-methoxyphenyl)methyl, 4-(4'-bromophenacyloxy)-phenyldiphenylmethyl, 4,4',4"-tris(4,5-dichlorophthalimidophenyl)methyl, 4,4',4"-tris(levulinoyloxyphenyl)methyl, 4,4'-dimethoxy-3"-[N-(imidazolylmethyl)]trityl, 4,4'-dimethoxy-3"-[N-(imidazolylethyl)carbamoyl]trityl, 1,1-bis(4-methoxyphenyl)-1'-pyrenylmethyl, 4-(17-tetrabenzo[a,c,g,l]fluorenylmethyl)-4,4'-dimethoxytrityl, 9-anthryl, 9-(9-phenyl)xanthenyl, 9-(9-phenyl-10-oxo)anthryl and the like;

c) Trimethylsilyl, triethylsilyl, triisopropylsilyl, dimethylisopropylsilyl, diethylisopropylsilyl, dimethylhexylsilyl, tert-butyldimethylsilyl, tert-butyldiphenylsilyl, tribenzylsilyl, tri-p-xylylsilyl, triphenylsilyl, diphenylmethylsilyl, di-tert-butylmethylsilyl, tris (trimethylsilyl)silyl, (2-hydroxystyryl)dimethylsilyl, (2-hydroxystyryl)diisopropylsilyl, tert-butylmethoxyphenylsilyl, tert-butoxydiphenylsilyl and the like;

d) —C(O)R$_{20}$, where R$_{20}$ is selected from alkyl, substituted alkyl, aryl and more specifically R$_{20}$=hydrogen, methyl, ethyl, tert-butyl, adamantyl, crotyl, chloromethyl, dichloromethyl, trichloromethyl, trifluoromethyl, methoxymethyl, triphenylmethoxymethyl, phenoxymethyl, 4-chlorophenoxymethyl, phenylmethyl, diphenylmethyl, 4-methoxycrotyl, 3-phenylpropyl, 4-pentenyl, 4-oxopentyl, 4,4-(ethylenedithio)pentyl, 5-[3-bis (4-methoxyphenyl)hydroxymethylphenoxy]-4-oxopentyl, phenyl, 4-methylphenyl, 4-nitrophenyl, 4-fluorophenyl, 4-chlorophenyl, 4-methoxyphenyl, 4-phenylphenyl, 2,4,6-trimethylphenyl, α-naphthyl, benzoyl and the like;

e) —C(O)OR$_{20}$, where R$_{20}$ is selected from alkyl, substituted alkyl, aryl and more specifically R$_{20}$=methyl, methoxymethyl, 9-fluorenylmethyl, ethyl, 2,2,2-trichloromethyl, 1,1-dimethyl-2,2,2-trichloroethyl, 2-(trimethylsilyl)ethyl, 2-(phenylsulfonyl)ethyl, isobutyl, tert-Butyl, vinyl, allyl, 4-nitrophenyl, benzyl, 2-nitrobenzyl, 4-nitrobenzyl, 4-methoxybenzyl, 2,4-dimethoxybenzyl, 3,4-dimethoxybenzyl, 2-(methylthiomethoxy)ethyl, 2-dansenylethyl, 2-(4-nitrophenyl)ethyl, 2-(2,4-dinitrophenyl)ethyl, 2-cyano-1-phenylethyl, thiobenzyl, 4-ethoxy-1-naphthyl and the like.

The definition of "amino protecting group" includes but is not limited to:

a) 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 1-methyl-1-(triphenylphosphonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoromethyl)-6-chromonylmethyl, m-nitrophenyl, 3.5-dimethoxybenzyl, 1-methyl-1-(3,5-dimethoxyphenyl)ethyl, o-nitrobenzyl, α-methylnitropiperonyl, 3,4-dimethoxy-6-nitrobenzyl, N-benzenesulfenyl, N-o-nitrobenzenesulfenyl, N-2,4-dinitrobenzenesulfenyl, N-pentachlorobenzenesulfenyl. N-2-nitro-4-methoxybenzenesulfenyl, N-triphenylmethylsulfenyl, N-1-(2,2,2-trifluoro-1,1-diphenyl)ethylsulfenyl, N-3-nitro-2-pyridinesulfenyl, N-p-toluenesulfonyl, N-benzenesulfonyl, N-2,3,6-trimethyl-4-methoxybenzenesulfonyl, N-2,4,6-trimethoxybenzene-sulfonyl, N-2,6-dimethyl-4-methoxybenzenesulfonyl, N-pentamethylbenzenesulfonyl, N-2,3,5,6-tetramethyl-4-methoxybenzenesulfonyl and the like;

b) —C(O)OR$_{20}$, where R$_{20}$ is selected from alkyl, substituted alkyl, aryl and more specifically R$_{20}$=methyl, ethyl, 9-fluorenylmethyl, 9-(2-sulfo)fluorenylmethyl. 9-(2,7-dibromo)fluorenylmethyl, 17-tetrabenzo[a,c,g,i]fluorenylmethyl. 2-chloro-3-indenylmethyl, benz[f]inden-3-ylmethyl, 2,7-di-t-butyl-[9-(10,10-dioxo-10,10,10,10-tetrahydrothloxanthyl)]methyl, 1,1-dioxobenzo[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-tert-butylphenyl)-1-methylethyl, 2-(2'-pyridyl)ethyl, 2-(4'-pyridyl)ethyl, 2,2-bis (4'-nitrophenyl)ethyl, N-(2-pivaloylamino)-1,1-dimethylethyl, 2-[(2-nitrophenyl)dithio]-1-phenylethyl, tert-butyl, 1-adamantyl, 2-adamantyl, Vinyl, allyl, 1-Isopropylallyl, cinnamyl. 4-nitrocinnamyl, 3-(3'-pyridyl)prop-2-enyl, 8-quinolyl, N-Hydroxypiperidinyl, alkyldithio, benzyl, p-methoxybenzyl, p-nitrobenzyl, p-bromobenzyl. p-chlorobenzyl, 2,4-dichlorobenzyl, 4-methylsulfinylbenzyl, 9-anthrylmethyl, diphenylmethyl, tert-amyl, S-benzyl thiocarbamate, butynyl, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N'-dimethylcarboxamido)benzyl, 1,1-dimethyl-3-(N,N'-dimethylcarboxamido)propyl, 1,1-dimethylpropynyl, di(2-pyridyl)methyl, 2-furanylmethyl, 2-Iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1-methyl-1-4'-pyridylethyl, phenyl, p-(phenylazo)benzyl, 2,4,6-trimethylphenyl, 4-(trimethylammonium)benzyl, 2,4,6-trimethylbenzyl and the like.

The definition of "carboxyl protecting group" includes but is not limited to:

2-N-(morpholino)ethyl, choline, methyl, methoxyethyl, 9-Fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropylsilylmethyl, cyanomethyl, acetol, p-bromophenacyl. α-methylphenacyl, p-methoxyphenacyl, desyl, carboxamidomethyl, p-azobenzenecarboxamido-methyl, N-phthalimidomethyl, (methoxyethoxy)ethyl, 2,2,2-trichloroethyl, 2-fluoroethyl, 2-chloroethyl, 2-bromoethyl, 2-iodoethyl, 4-chlorobutyl, 5-chloropentyl, 2-(trimethylsilyl)ethyl, 2-methylthioethyl, 1,3-dithianyl-2-methyl, 2-(p-nitrophenylsulfenyl)ethyl 2-(p-toluenesulfonyl)ethyl, 2-(2-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl, 2-cyanoethyl, heptyl, tert-butyl, 3-methyl-3-pentyl, dicyclopropylmethyl, 2,4-dimethyl-3-pentyl, cyclopentyl, cyclohexyl, allyl, methallyl, 2-methylbut-3-en-2-yl, 3-methylbut-2-(prenyl), 3-buten-1-yl, 4-(trimethylsilyl)-2-buten-1-yl, cinnamyl, α-methylcinnamyl, propargyl, phenyl, 2,6-dimethylphenyl, 2,6-diisopropylphenyl, 2,6-di-tert-butyl-4-methylphenyl, 2,6-di-tert-butyl-4-methoxyphenyl, p-(methylthio)phenyl, pentafluorophenyl, benzyl, triphenylmethyl, diphenylmethyl, bis (o-nitrophenyl)methyl, 9-anthrylmethyl, 2-(9,10-dioxo)anthrylmethyl. 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2.6-dimethoxybenzyl, 4-(methylsulfinyl)benzyl, 4-Sulfobenzyl, 4-azidomethoxybenzyl, 4-{a/-[1-(4,4-dimethyl-2,6-dioxocyclohexylidene)-3-methylbutyl]amino}benzyl, piperonyl, 4-picolyl, trimethylsilyl, triethylsilyl, tert-butyldimethylsilyl, isopropyldimethylsilyl, phenyldimethylsilyl, di-tert-butylmethylsilyl, triisopropylsilyl and the like.

The term "Amino acid" refers to any of the naturally occurring amino acids, as well as synthetic analogs and derivatives thereof. Alpha-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine), substituted arylalkyl (e.g., as in tyrosine), heteroarylalkyl (e.g., as in tryptophan, histidine) and the like. One of skill in the art will appreciate that the term "amino acid" can also include beta-, gamma-, delta-, omega-amino acids, and the like. Unnatural amino acids are also known in the art, as set forth in, Natchus, M. gram. Organic Synthesis: Theory and Applications (2001), 5, 89-196; Ager, D. J. Current Opinion in Drug Discovery & Development (2001), 4 (6), 800; Reginato, gram. Recent Research Developments in Organic Chemistry (2000), 4 (Pt. 1), 351-359; Dougherty, D. A. Current Opinion in Chemical Biology (2000), 4 (6), 645-652; Lesley, S. A. Drugs and the Pharmaceutical Sciences (2000), 101 (Peptide and Protein Drug Analysis), 191-205; Pojitkov, A. E. Journal of Molecular Catalysis B: Enzymatic (2000), 10 (1-3), 47-55; Ager, D. J. Speciality Chemicals (1999), 19 (1), 10-12, and all references cited therein. Stereoisomers (e.g., D-amino acids) of the twenty conventional amino acids, unnatural amino acids such as alpha, alpha-disubstituted amino acids and other unconventional amino acids may also be suitable components for compounds of the present invention. Examples of unconventional amino acids include: 4-hydroxyproline, 3-methylhistidine, 5-hydroxylysine, and other similar amino acids and imino acids (e.g., 4-hydroxyproline).

The term "N-protected amino acid" refers to any amino acid which has a protecting group bound to the nitrogen of the amino functionality. This protecting group prevents reactions from occurring at the amino functional group and can be removed by conventional chemical or enzymatic steps to reestablish the amino functional group. The particular protecting group employed is not critical.

The term "O-protected amino acid" refers to any amino acid which has a protecting group bound to the oxygen of the carboxyl functionality. This protecting group prevents reactions from occurring at the carboxyl functional group and can be removed by conventional chemical or enzymatic steps to reestablish the carboxyl functional group. The particular protecting group employed is not critical.

The term "Prodrug" refers to an agent that is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. A prodrug may be converted into the parent drug by various mechanisms, including enzymatic processes and metabolic hydrolysis. See Harper, "Drug Latentiation" in Jucker, ed. Progress in Drug Research 4:221-294 (1962); Morozowich et al., "Application of Physical Organic Principles to Prodrug Design" in E. B. Roche ed. Design of Biopharmaceutical Properties through Prodrugs and Analogs, APHA Acad. Pharm. Sci. (1977); Bioreversible Carriers in Drug in Drug Design, Theory and Application, E. B. Roche, ed., APHA Acad. Pharm. Sci. (1987); Design of Prodrugs, H. Bundgaard, Elsevier (1985); Wang et al. "Prodrug approaches to the improved delivery of peptide drug" in Curr. Pharm. Design. 5 (4):265-287 (1999); Pauletti et al. (1997) Improvement in peptide bioavailability: Peptidomimetics and Prodrug Strategies, Adv. Drug. Delivery Rev. 27:235-256; Mizen et al. (1998) "The Use of Esters as Prodrugs for Oral Delivery of beta.-Lactam antibiotics," Pharm. Biotech. 11:345-365; Gaignault et al. (1996) "Designing Prodrugs and Bioprecursors I. Carrier Prodrugs," Pract. Med. Chem. 671-696; Asgharnejad, "Improving Oral Drug Transport", in Transport Processes in Pharmaceutical Systems, gram. L. Amidon, P. I. Lee and E. M. Topp, Eds., Marcell Dekker, p. 185-218 (2000); Balant et al., "Prodrugs for the improvement of drug absorption via different routes of administration", Eur. J. Drug Metab. Pharmacokinet., 15 (2): 143-53 (1990); Balimane and Sinko, "Involvement of multiple transporters in the oral absorption of nucleoside analogues", Adv. Drug Delivery Rev., 39 (1-3): 183-209 (1999); Browne, "Fosphenyloin (Cerebyx)", Clin. Neuropharmacol. 20 (1): 1-12 (1997); Bundgaard, "Bioreversible derivatization of drugs—principle and applicability to improve the therapeutic effects of drugs", Arch. Pharm. Chemi 86 (1): 1-39 (1979); Bundgaard H. "Improved drug delivery by the prodrug approach", Controlled Drug Delivery 17: 179-96 (1987); Bundgaard H. "Prodrugs as a means to improve the delivery of peptide drugs", Adv. Drug Delivery Rev. 8 (1): 1-38 (1992); Fleisher et al. "Improved oral drug delivery: solubility limitations overcome by the use of prodrugs", Adv. Drug Delivery Rev. 19 (2): 115-130 (1996); Fleisher et al. "Design of prodrugs for improved gastrointestinal absorption by intestinal enzyme targeting", Methods Enzymol. 112 (Drug Enzyme Targeting, Pt. A): 360-81, (1985); Farquhar D, et al., "Biologically Reversible Phosphate-Protective Groups", J. Pharm. Sci., 72 (3): 324-325 (1983); Freeman S, et al., "Bioreversible Protection for the Phospho Group: Chemical Stability and Bioactivation of Di(4-acetoxy-benzyl) Methylphosphonate with Carboxyesterase," J. Chem. Soc., Chem. Commun., 875-877 (1991); Friis and Bundgaard, "Prodrugs of phosphates and phosphonates: Novel lipophilic alpha-acyloxyalkyl ester derivatives of phosphate- or phosphonate containing drugs masking the negative charges of these groups", Eur. J. Pharm. Sci. 4: 49-59 (1996); Gangwar et al., "Prodrug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45 (6): 866-94 (1993); Sinhababu and Thakker, "Prodrugs of anticancer agents", Adv. Drug Delivery Rev. 19 (2): 241-273 (1996); Stella et al., "Prodrugs. Do they have advantages in clinical practice?", Drugs 29 (5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39 (1-3): 117-151 (1999); Taylor, "Improved passive oral drug delivery via prodrugs", Adv. Drug Delivery Rev., 19 (2): 131-148 (1996); Valentino and Borchardt, "Prodrug strategies to enhance the intestinal absorption of peptides", Drug Discovery Today 2 (4): 148-155 (1997); Wiebe and Knaus, "Concepts for the design of anti-HIV nucleoside prodrugs for treating cephalic HIV infection", Adv. Drug Delivery Rev.: 39 (1-3):63-80 (1999); Waller et al., "Prodrugs", Br. J. Clin. Pharmac. 28: 497-507 (1989).

The terms "halogen", "halide" or "halo" include fluorine, chlorine, bromine, and iodine.

The terms "alkyl" and "substituted alkyl" are interchangeable and include substituted and unsubstituted $C_1$-$C_{10}$ straight chain saturated aliphatic hydrocarbon groups, substituted and unsubstituted $C_2$-$C_{10}$ straight chain unsaturated aliphatic hydrocarbon groups, substituted and unsubstituted $C_4$-$C_{10}$ branched saturated aliphatic hydrocarbon groups, substituted and unsubstituted $C_4$-$C_{10}$ branched unsaturated aliphatic hydrocarbon groups, substituted and unsubstituted $C_3$-$C_8$ cyclic saturated aliphatic hydrocarbon groups, substituted and unsubstituted $C_5$-$C_8$ cyclic unsaturated aliphatic hydrocarbon groups having the specified number of carbon atoms. For example, the definition of "alkyl" shall include but is not limited to: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, adamantyl, norbornyl and the like. Alkyl substituents are independently selected from the group comprising halogen, —OH, —SH, —NH$_2$, —CN, —NO$_2$, =O, =CH$_2$, trihalomethyl, carbamoyl, arylC$_{0-10}$alkyl, heteroarylC$_{0-10}$alkyl, C$_{1-10}$alkyloxy, arylC$_{0-10}$alkyloxy, C$_{1-10}$alkylthio, arylC$_{0-10}$alkylthio, C$_{1-10}$alkylamino, arylC$_{0-10}$alkylamino, N-aryl-N-C$_{0-10}$alkylamino, C$_{1-10}$alkylcarbonyl, arylC$_{0-10}$alkylcarbonyl, C$_{1-10}$alkylcarboxy, arylC$_{0-10}$alkylcarboxy, C$_{1-10}$alkylcarbonylamino, arylC$_{0-10}$alkylcarbonylamino, tetrahydrofuryl, morpholinyl, piperazinyl, hydroxypyronyl, —C$_{0-10}$alkylCOOR$_{21}$ and —C$_{0-10}$alkylCONR$_{22}$R$_{23}$ wherein R$_{21}$, R$_{22}$ and R$_{23}$ are independently selected from hydrogen, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined herein.

The term "alkyloxy" (e.g. methoxy, ethoxy, propyloxy, allyloxy, cyclohexyloxy) represents a substituted or unsubstituted alkyl group as defined above having the indicated number of carbon atoms attached through an oxygen bridge. The term "alkyloxyalkyl" represents an alkyloxy group attached through an alkyl or substituted alkyl group as defined above having the indicated number of carbon atoms.

The term "alkylthio" (e.g. methylthio, ethylthio, propylthio, cyclohexenylthio and the like) represents a substituted or unsubstituted alkyl group as defined above having the indicated number of carbon atoms attached through a sulfur bridge. The term "alkylthioalkyl" represents an alkylthio group attached through an alkyl or substituted alkyl group as defined above having the indicated number of carbon atoms.

The term "alkylamino" (e.g. methylamino, diethylamino, butylamino, N-propyl-N-hexylamino, (2-cyclopentyl)propylamino, hexenylamino, and the like) represents one or two substituted or unsubstituted alkyl groups as defined above having the indicated number of carbon atoms attached through an amine bridge. The substituted or unsubstituted alkyl groups maybe taken together with the nitrogen to which they are attached forming a saturated cyclic or unsaturated cyclic system containing 3 to 10 carbon atoms with at least one substituent as defined above. The term "alkylaminoalkyl" represents an alkylamino group attached through a substituted or unsubstituted alkyl group as defined above having the indicated number of carbon atoms.

The term "alkylhydrazino" (e.g. methylhydrazino, diethylhydrazino, butylhydrazino, (2-cyclopentyl)propylhydrazino, cyclohexanehydrazino, and the like) represents one or two substituted or unsubstituted alkyl groups as defined above having the indicated number of carbon atoms attached through a nitrogen atom of a hydrazine bridge. The substituted or unsubstituted alkyl groups maybe taken together with the nitrogen to which they are attached forming a saturated cyclic or unsaturated cyclic system containing 3 to 10 carbon atoms with at least one substituent as defined above. The term "alkylhydrazinoalkyl" represents an alkylhydrazino group attached through a substituted or unsubstituted alkyl group as defined above having the indicated number of carbon atoms.

The term "alkylcarbonyl" (e.g. cyclooctylcarbonyl, pentylcarbonyl, 3-hexenylcarbonyl and the like) represents a substituted or unsubstituted alkyl group as defined above having the indicated number of carbon atoms attached through a carbonyl group. The term "alkylcarbonylalkyl" represents an alkylcarbonyl group attached through a substituted or unsubstituted alkyl group as defined above having the indicated number of carbon atoms.

The term "alkylcarboxy" (e.g. heptylcarboxy, cyclopropylcarboxy, 3-pentenylcarboxy and the like) represents an alkylcarbonyl group as defined above wherein the carbonyl is in turn attached through an oxygen. The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonyl-aminomethyl, methylcarbonylaminophenyl and the like) represents an alkylcarbonyl group as defined above wherein the carbonyl is in turn attached through the nitrogen atom of an amino group. The nitrogen group may itself be substituted with a substituted or unsubstituted alkyl or aryl group. The term "alkylcarbonylaminoalkyl" represents an alkylcarbonylamino group attached through a substituted or unsubstituted alkyl group as defined above having the indicated number of carbon atoms.

The term "alkylcarbonylhydrazino" (e.g. ethylcarbonylhydrazino, tert-butylcarbonylhydrazino and the like) represents an alkylcarbonyl group as defined above wherein the carbonyl is in turn attached through the nitrogen atom of a hydrazino group.

The term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from the group comprising halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$CO_{0-10}$alkyl, N-aryl-N-$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{0-10}$alkylcarbonylamino$C_{0-10}$alkyl, aryl$C_{0-10}$alkylcarbonylamino$C_{0-10}$alkyl, —$C_{0-10}$alkyl COOR$_{21}$, and —$C_{0-10}$alkylCONR$_{22}$R$_{23}$ wherein R$_{21}$, R$_{22}$ and R$_{23}$ are independently selected from hydrogen, alkyl, aryl or R$_{22}$ and R$_{23}$ are taken together with the nitrogen to which they are attached forming a saturated cyclic or unsaturated cyclic system containing 3 to 8 carbon atoms with at least one substituent as defined above.

The definition of "aryl" includes but is not limited to phenyl, biphenyl, naphthyl, dihydronaphthyl, tetrahydronaphthyl, indenyl, indanyl, azulenyl, anthryl, phenanthryl, fluorenyl, pyrenyl and the like.

The term "arylalkyl" (e.g. (4-hydroxyphenyl)ethyl, (2-aminonaphthyl)hexenyl and the like) represents an aryl group as defined above attached through a substituted or unsubstituted alkyl group as defined above having the indicated number of carbon atoms.

The term "arylcarbonyl" (e.g. 2-thiophenylcarbonyl, 3-methoxyanthrylcarbonyl and the like) represents an aryl group as defined above attached through a carbonyl group.

The term "arylalkylcarbonyl" (e.g. (2,3-dimethoxyphenyl)propylcarbonyl, (2-chloronaphthyl)pentenyl-carbonyl and the like) represents an arylalkyl group as defined above wherein the alkyl group is in turn attached through a carbonyl.

The term "aryloxy" (e.g. phenoxy, naphthoxy, 3-methylphenoxy, and the like) represents an aryl or substituted aryl group as defined above having the indicated number of carbon atoms attached through an oxygen bridge. The term "aryloxyalkyl" represents an aryloxy group attached through a substituted or unsubstituted alkyl group as defined above having the indicated number of carbon atoms.

The term "arylthio" (e.g. phenylthio, naphthylthio, 3-bromophenylthio, and the like) represents an aryl or substituted aryl group as defined above having the indicated number of carbon atoms attached through a sulfur bridge. The term "arylthioalkyl" represents an arylthio group attached through a substituted or unsubstituted alkyl group as defined above having the indicated number of carbon atoms.

The term "arylamino" (e.g. phenylamino, diphenylamino, naphthylamino, N-phenyl-N-naphthylamino, o-methylphenylamino, p-methoxyphenylamino, and the like) represents one or two aryl groups as defined above having the indicated number of carbon atoms attached through an amine bridge. The term "arylaminoalkyl" represents an arylamino group attached through a substituted or unsubstituted alkyl group as defined above having the indicated number of carbon atoms. The term "arylalkylamino" represents an aryl group attached through an alkylamino group as defined above having the indicated number of carbon atoms. The term "N-aryl-N-alkylamino" (e.g. N-phenyl-N-methylamino, N-naphthyl-N-butylamino, and the like) represents one aryl and one a substituted or unsubstituted alkyl group as defined above having the indicated number of carbon atoms independently attached through an amine bridge.

The term "arylhydrazino" (e.g. phenylhydrazino, naphthylhydrazino, 4-methoxyphenylhydrazino, and the like) represents one or two aryl groups as defined above having the indicated number of carbon atoms attached through a hydrazine bridge. The term "arylhydrazinoalkyl" represents an arylhydrazino group attached through a substituted or unsubstituted alkyl group as defined above having the indicated number of carbon atoms. The term "arylalkylhydrazino" represents an aryl group attached through an alkylhydrazino group as defined above having the indicated number of carbon atoms. The term "N-aryl-N-alkylhydrazino" (e.g. N-phenyl-N-methylhydrazino, N-naphthyl-N-butylhydrazino, and the like) represents one aryl and one a substituted or unsubstituted alkyl group as defined above having the indicated number of carbon atoms independently attached through an amine atom of a hydrazine bridge.

The term "arylcarboxy" (e.g. phenylcarboxy, naphthylcarboxy, 3-fluorophenylcarboxy and the like) represents an arylcarbonyl group as defined above wherein the carbonyl is in turn attached through an oxygen bridge. The term "arylcarboxyalkyl" represents an arylcarboxy group attached through a substituted or unsubstituted alkyl group as defined above having the indicated number of carbon atoms.

The term "arylcarbonylamino" (e.g. phenylcarbonylamino, naphthylcarbonylamino, 2-methylphenylcarbonylamino and the like) represents an arylcarbonyl group as defined above wherein the carbonyl is in turn attached through the nitrogen atom of an amino group. The nitrogen group may itself be substituted with an a substituted or unsubstituted alkyl or aryl group. The term "arylcarbonylaminoalkyl" represents an arylcarbonylamino group attached through a substituted or unsubstituted alkyl group as defined above having the indicated number of carbon atoms. The nitrogen group may itself be substituted with a substituted or unsubstituted alkyl or aryl group.

The term "arylcarbonylhydrazino" (e.g. phenylcarbonylhydrazino, naphthylcarbonylhydrazino, and the like) represents an arylcarbonyl group as defined above wherein the carbonyl is in turn attached through the nitrogen atom of a hydrazino group.

The terms "heteroaryl", "heterocycle" or "heterocyclic" refers to a monovalent unsaturated group having a single ring or multiple condensed rings, from 1 to 8 carbon atoms and from 1 to 4 hetero atoms selected from nitrogen, sulfur or oxygen within the ring. The heteroaryl groups in this invention can be optionally substituted with 1 to 3 substituents selected from the group comprising: halogen, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N-$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_{21}$, and —CO$_{10}$alkylCONR$_{22}$R$_{23}$ wherein R$_{21}$, R$_{22}$ and R$_{23}$ are independently selected from hydrogen, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined above.

The definition of "heteroaryl" includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl, 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5]tetrazinanyl-3,6-dione, dihydro-pyrimidinyl-2,4-dione, pyrimidinyl-2,4,6-trione and the like. For the purposes of this application, the terms "heteroaryl", "heterocycle" or "heterocyclic" do not include carbohydrate rings (i.e. mono- or oligosaccharides).

The term "saturated heterocyclic" represents an unsubstituted, mono-, di- or trisubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl and the like).

The saturated heterocyclic substituents are independently selected from the group comprising halo, —OH, —SH, —CN, —NO$_2$, trihalomethyl, hydroxypyronyl, $C_{1-10}$alkyl, aryl$C_{0-10}$alkyl, $C_{0-10}$alkyloxy$C_{0-10}$alkyl, aryl$C_{0-10}$alkyloxy$C_{0-10}$alkyl, $C_{0-10}$alkylthio$C_{0-10}$alkyl, aryl$C_{0-10}$alkylthio$C_{0-10}$alkyl, $C_{0-10}$alkylamino$C_{0-10}$alkyl, aryl$C_{0-10}$alkylamino$C_{0-10}$alkyl, N-aryl-N-$C_{0-10}$alkylamino$C_{0-10}$alkyl, $C_{1-10}$alkylcarbonyl$C_{0-10}$alkyl, aryl$C_{0-10}$alkylcarbonyl$C_{0-10}$alkyl, $C_{1-10}$alkylcarboxy$C_{0-10}$alkyl, aryl$C_{0-10}$alkylcarboxy$C_{0-10}$alkyl, $C_{1-10}$alkylcarbonylamino$C_{0-10}$alkyl, aryl$C_{0-10}$alkylcarbonylamino$C_{0-10}$alkyl, —$C_{0-10}$alkylCOOR$_{21}$, and —$C_{0-10}$alkylCONR$_{22}$R$_{23}$ wherein R$_{21}$, R$_{22}$ and R$_{23}$ are independently selected from hydrogen, alkyl, aryl, or R$_{22}$ and R$_{23}$ are taken together with the nitrogen to which they are attached forming a saturated cyclic or unsaturated cyclic system containing 3 to 8 carbon atoms with at least one substituent as defined above.

The definition of saturated heterocyclic includes but is not limited to pyrrolidinyl, pyrazolidinyl, piperidinyl, 1,4-dioxanyl, morpholinyl, 1,4-dithienyl, thiomorpholinyl, piperazinyl, quinuclidinyl, and the like.

The term "alpha-beta-unsaturated carbonyl" refers to a molecule that has a carbonyl group directly attached to a double or triple bonded cabon and which would be obvious to one of ordinary skill and knowledge in the art. The definition of alpha-beta-unsaturated carbonyl includes but is not limited to acrolein, methyl vinyl ketone, and the like.

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

As used herein, the term "modulation" or "modulating" refers to the alteration of the catalytic activity of an enzyme or receptor in vitro and/or in vivo.

"In vitro" refers to procedures performed in an artificial environment such as, such as for example, without limitation, in a test tube or culture medium. The skilled artisan will understand that, for example, an isolated enzyme and/or receptor may be contacted with a modulator in an in vitro environment. Alternatively, an isolated cell may be contacted with a modulator in an in vitro environment.

As used herein, "in vivo" refers to procedures performed within a living organism such as, without limitation, a mouse, rat, rabbit, ungulate, bovine, equine, porcine, canine, feline, primate, or human.

The term "organism" refers to any living entity comprised of at least one cell. A living organism can be as simple as, for example, a single eukaryotic cell or as complex as a mammal, including a human being.

The term "therapeutically effective amount" as used herein refers to that amount of the compound being administered which will relieve to some extent one or more of the symptoms of the disorder being treated. For example, in reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

"Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or a pharmaceutically acceptable salts thereof, with other chemical components, such as physiologically acceptable carriers and excipients. The purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

A "subject" of treatment is an animal, such as a mammal, including a human. Animals subject to treatment include, for example, fish, birds, and mammals such as cows, sheep, pigs, horses, dogs, cats and the like.

A "therapeutic treatment" is a treatment administered to a subject who exhibits signs of pathology for the purpose of diminishing or eliminating those signs.

Preferred compounds of the present invention also include pharmaceutically acceptable salts of the compounds of the above formulae. A "pharmaceutically acceptable salt" is a salt that can be formulated into a compound for pharmaceutical use including, such as for example, metal salts (sodium, potassium, magnesium, calcium, etc.) and salts of ammonia or organic amines.

In one aspect, the invention relates to pharmaceutical compositions comprising at least one of the compounds of the invention, as well as pharmaceutically acceptable prodrugs and salts of such compounds, in a pharmaceutically acceptable vehicle, for enteral, parenteral, topical or ocular administration.

In another aspect, the invention relates to pharmaceutical compositions comprising at least one of the compounds of the invention, as well as pharmaceutically acceptable prodrugs and salts of such compounds, in a pharmaceutically acceptable vehicle, for the prophylactic and therapeutic treatment of subjects as described herein.

In another aspect, the invention relates to pharmaceutical compositions comprising at least one of the compounds of the invention, as well as pharmaceutically acceptable prodrugs and salts of such compounds, in a pharmaceutically acceptable vehicle, for inhibiting oxidation in biological materials. The methods involve contacting the biological material with an effective amount of the compound. In the therapeutic methods of this invention, a pharmacologically effective amount of the compound is administered to a subject suffering from a pathological condition responsive to inhibition of oxidation. In the prophylactic methods of this invention a pharmaceutically effective amount of the compound is administered to a subject at risk of developing a disease as a result of exposure to oxidative stress.

In another aspect, the invention relates to pharmaceutical compositions comprising at least one of the compounds of the invention, as well as pharmaceutically acceptable prodrugs and salts of such compounds, in a pharmaceutically acceptable vehicle, for the treatment or prevention of conditions having an inflammatory component. A pharmacologically effective amount of the compound is administered to a subject suffering from, or at risk of suffering from, a pathological condition that can be improved by inhibiting inflammation. In general, an effective dose is about 100 milligram to about 1 gram taken orally per day.

In another aspect, the invention relates to pharmaceutical compositions comprising at least one of the compounds of the invention, as well as pharmaceutically acceptable prodrugs and salts of such compounds, in a pharmaceutically acceptable vehicle, for treating arthritis, both rheumatoid arthritis and osteoarthritis. The compounds preferably are delivered orally or transdermally for this purpose. A pharmacologically effective amount of the agent taken orally is about 50 milligram to about 2 gram daily.

In yet another aspect, the invention relates to pharmaceutical compositions comprising at least one of the compounds of the invention, as well as pharmaceutically acceptable prodrugs and salts of such compounds, in a pharmaceutically acceptable vehicle, for the prophylactic or therapeutic treatment of respiratory disorders that involve an inflammatory component. Examples of respiratory diseases that can be treated with these compounds include acid aspiration, adult/infant respiratory distress syndrome, airway obstructive disease, asthma, bronchiolitis, bronchopulmonary dysplasia, cancer, chronic obstructive pulmonary disease ("COPD"), cystic fibrosis, emphysema, HIV-associated lung disease, idiopathic pulmonary fibrosis, immune-complex-mediated lung injury, exposure to an oxidizing agent, ischemia-reperfusion injury, mineral dust pneumoconiosis, drug-induced lung disease, silo-filler's disease and the like. In the treatment of respiratory conditions, the compound is preferably delivered by inhalation. The compound can be delivered as an aerosol, mist or powder. An effective amount for delivery by inhalation is about 0.1 milligram to 10 milligram per inhalation, several times daily. The compound also can be delivered orally in amounts of about 50 milligram to about 2 gram daily.

In another aspect, the invention relates to pharmaceutical compositions comprising at least one of the compounds of the invention, as well as pharmaceutically acceptable prodrugs and salts of such compounds, in a pharmaceutically acceptable vehicle, for the treatment of nervous system disorders. Examples of such neurodegenerative conditions of the nervous system include Friedrich's disease, Parkinson's disease, Alzheimer's disease, Huntington's disease, Pick disease, amyotrophic lateral sclerosis, multiple sclerosis and the like.

In another aspect, the invention relates to pharmaceutical compositions comprising at least one of the compounds of the invention, as well as pharmaceutically acceptable prodrugs and salts of such compounds, in a pharmaceutically acceptable vehicle, for treating trauma to the central nervous system. Examples of such trauma include skull fracture and its resulting edema, concussion, contusion, brain hemorrhages, shearing lesions, subdural hematoma, epidural hematoma, spinal cord injury and the like. In the treatment of traumatic conditions of the central nervous system, the compound preferably is administered parenterally, such as by intravenous injection or injection directly into the central nervous system (i.e., intrathecally (IT) or into the brain). A pharmacologically effective amount of the compound is about 25 milligram to about 500 milligram i.v. or i.m. and about 5 milligram to about 100 milligram IT. The treatment of chronic neurodegenerative disease is best effected via oral administration of an effective amount of the compound, preferably 50 milligram to 2 gram daily.

In another aspect, the invention relates to pharmaceutical compositions comprising at least one of the compounds of the invention, as well as pharmaceutically acceptable prodrugs and salts of such compounds, in a pharmaceutically acceptable vehicle, for preventing/treating cardiovascular disease, including but not limited to ischemia-reperfusion dysfunction, atherosclerosis and restenosis following angioplasty. Oral, enteral or intravenous administration is useful for this purpose.

In another aspect, the invention relates to pharmaceutical compositions comprising at least one of the compounds of the invention, as well as pharmaceutically acceptable prodrugs and salts of such compounds, in a pharmaceutically acceptable vehicle, for the treatment of cancer or as adjuvants in the treatment of cancer. Co-administered with chemotherapeutic agents, they enhance cytotoxicity, thereby inhibiting the growth of tumors. In addition, they also inhibit oxidative damage that generally accompanies use of anti-cancer agents. Methods of treating cancer involve administering a pharmacologically effective amount of the compound to a subject prior to, during or after chemotherapy. The compounds are useful in the treatment of any cancer. However, they are particularly effective in the treatment of colorectal cancer and lung cancer. The compounds also are effective with chemotherapeutic agents that act by all known modes of action. In such treatments, the compounds preferably are delivered as a pharmaceutical composition in the form of an intravenous or intramuscular solution. However, other modes of delivery, such as enteral administration, also are useful. An effective amount of the agent is about 50 milligram to about 2 gram delivered daily over the course of the chemotherapy regimen.

In yet another aspect, the invention relates to pharmaceutical compositions containing the novel compounds of the invention in combination with other therapeutic agents and to methods of treating diseases and/or conditions using the same. Example of diseases and/or conditions include cancer, mammary cancer, prostate cancer, kidney cancer, Karposi's sarcoma, colon cancer, cervical cancer, lung cancer, cutaneous T-cell lymphoma, cancer of the head and neck, cancers of the aerodigestive pathway, skin cancer, bladder cancer, sarcomas, leukoplakias, acute promyelocytic leukemia and the like. Examples of other therapeutic agents include Busulfan, Carboplatin, Cisplatin, Cyclophosphamide, Cytosine arabinoside, Etoposide, 5-Fluorouracil, Melphalan, Methotrexate, Mitoxantrone, Taxol, Interferon, Fareston, Arzoxifene, Evista, Tamoxifen, and the like.

In another aspect, the invention relates to the use of pharmaceutical compositions comprising at least one of the compounds of the invention, as well as pharmaceutically acceptable prodrugs and salts of such compounds, in a pharmaceutically acceptable vehicle, as hypnotic agents for the same indications as 2,6-diisopropylphenol. Examples of such indications include inducing and/or maintaining general anaesthesia, use as a sedative and the like. The compound is administered in an amount effective to induce hypnosis. For use as a general anaesthetic, the compounds are preferably administered as an intravenous aqueous solution. However, they also can be administered by inhalation. For use as a sedative (such as for example, for the treatment of anxiety conditions), the compounds are preferably and effectively administered orally in amounts of about 10 milligram to 2 gram daily. However, they can also be administered by inhalation, intravenously or intramuscularly.

The novel compounds of this invention can be administered in similar amounts and in the same schedule as injectable emulsions of DIPRIVAN™. Dosage level of 2,6-diisopropylphenol for producing general anesthesia, both induction (for example about 2.0 to about 2.5 milligram/kg for an adult) and maintenance (for example, about 4 to about 12 milligram/kg/hr) and for producing a sedative effect (for example, about 0.3 to about 4.5 milligram/kg/hr) may be derived from the very substantial literature on 2,6-diisopropylphenol. The actual dosages of the 2,6-diisopropylphenol prodrugs, on a weight basis, may in some cases be higher than for 2,6-diisopropylphenol itself because (a) the molecular weights of the prodrugs are higher and (b) release of 2,6-diisopropylphenol from the prodrugs occurs at a finite rate. Furthermore, the anesthetist and/or physician would modify the dose to achieve the desired effect in any particular patient, in accordance with normal skill in the art.

In another aspect, the invention relates to pharmaceutical compositions comprising at least one of the compounds of the invention, as well as pharmaceutically acceptable prodrugs and salts of such compounds, in a pharmaceutically acceptable vehicle, for use as anti-emetics. Their administration is indicated in subjects at risk of vomiting or who feel nauseous. As an example, the compounds are usefully co-administered to subjects who are receiving treatments that induce nausea, such as various chemotherapy agents and surgical procedures. Accordingly, this invention provides methods for inhibiting nausea and vomiting by administering the compound to a subject in an amount effective to inhibit nausea and vomiting. In the prophylactic or therapeutic treatment of nausea or vomiting, the compounds preferably are delivered orally in a pharmaceutical composition. Accordingly, solid or liquid carriers are appropriate delivery vehicles. However, parenteral routes of administration, such as inhalation or injection, also are useful as well as topical and transdermal administration. For use as an anti-emetic, the compounds are effectively administered in amounts of about 50 milligram to about 2 gram.

In another aspect, the invention relates to pharmaceutical compositions comprising at least one of the compounds of the invention, as well as pharmaceutically acceptable pro-drugs and salts of such compounds, in a pharmaceutically acceptable vehicle, for use as anti-convulsives to prevent or relieve seizures including, such as for example, epileptic seizures. This invention provides methods for inhibiting convulsions comprising administering to a subject an amount of the compound effective to inhibit convulsions. In the prophylactic or therapeutic treatment of seizures the compounds preferably are delivered orally or parenterally. For use as an anti-convulsive, the compounds are effectively administered in amounts of about 50 milligram to about 2 gram daily.

In another aspect, the invention relates to pharmaceutical compositions comprising at least one of the compounds of the invention, as well as pharmaceutically acceptable pro-drugs and salts of such compounds, in a pharmaceutically acceptable vehicle, for use as anti-pruritics to prevent or relieve itching. This invention provides methods of inhibiting itching comprising administering the compound to a subject in an amount effective to inhibit itching. The compounds can treat both external and internal itching. The source of itching can be any disease or exposure to a pruritic agent, such as poison ivy. In the prophylactic or therapeutic treatment of itching, the compounds preferably are delivered topically in a pharmaceutical composition. Various creams and ointments are appropriate delivery vehicles. For use as an anti-pruritic, the compounds are effectively administered in amounts of about 50 milligram to about 2 gram daily or rubbed into the skin at about 0.01 to about 5 milligram per cm$^2$. Sub-sedative dose for pruritus may be achieved at between about one-quarter and about one-tenth the anesthetic dose.

Invention compounds having structure A include but are not limited to:

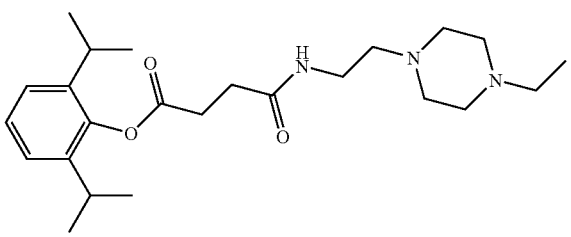

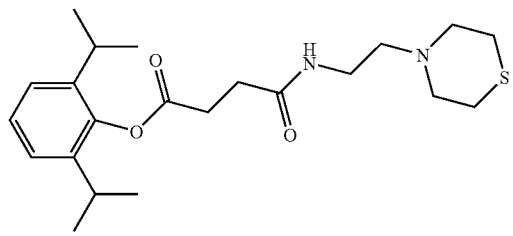

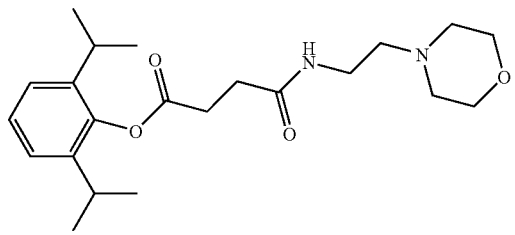

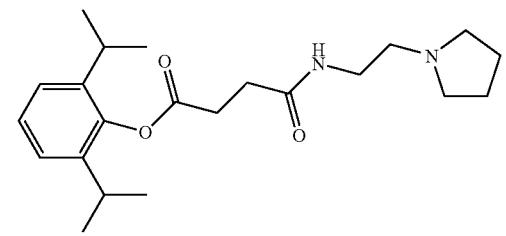

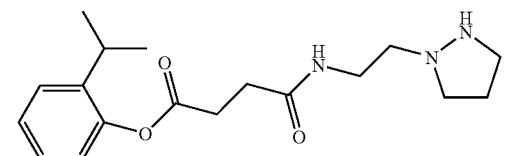

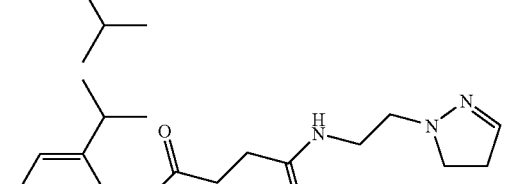

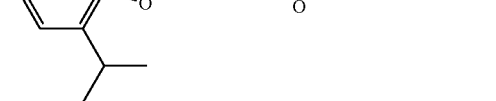

-continued

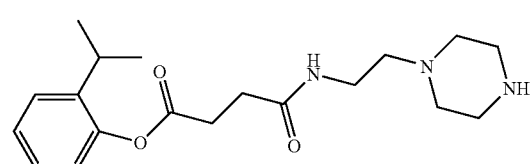

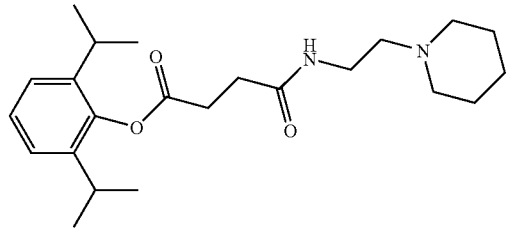

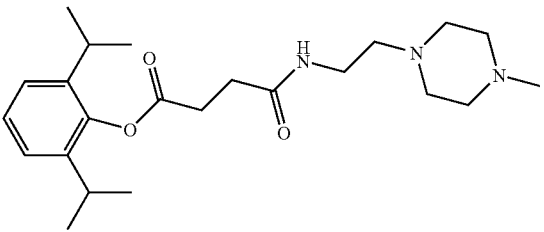

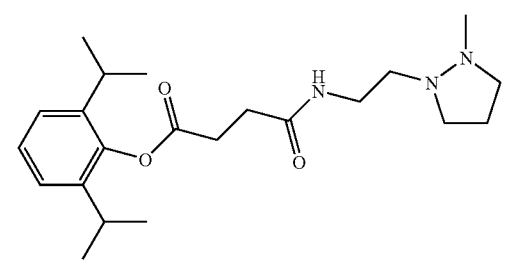

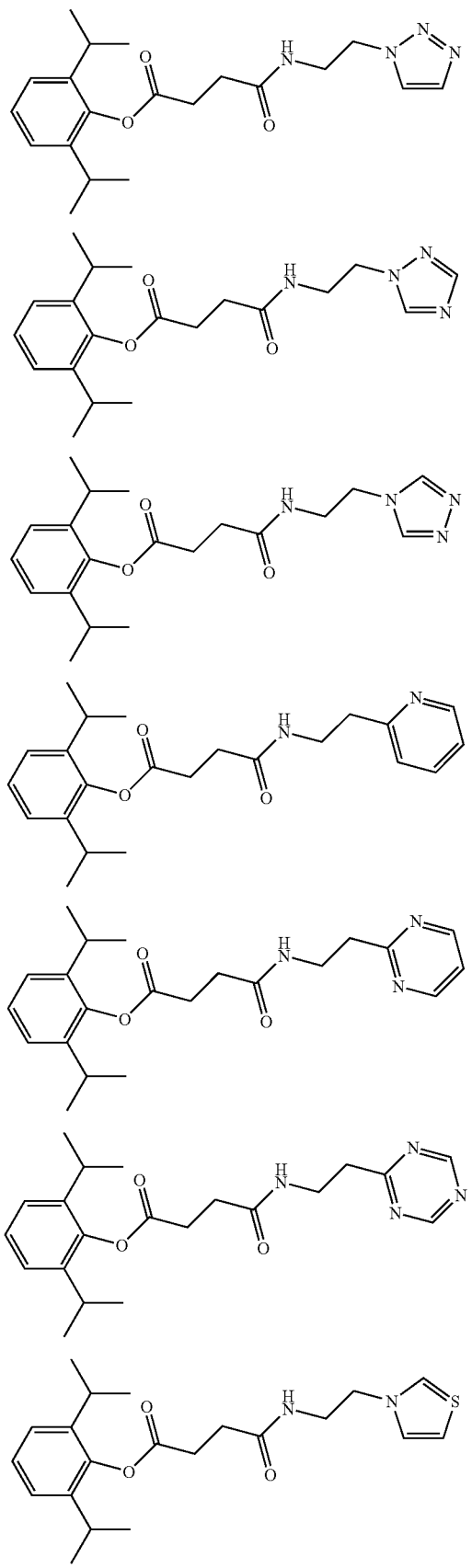
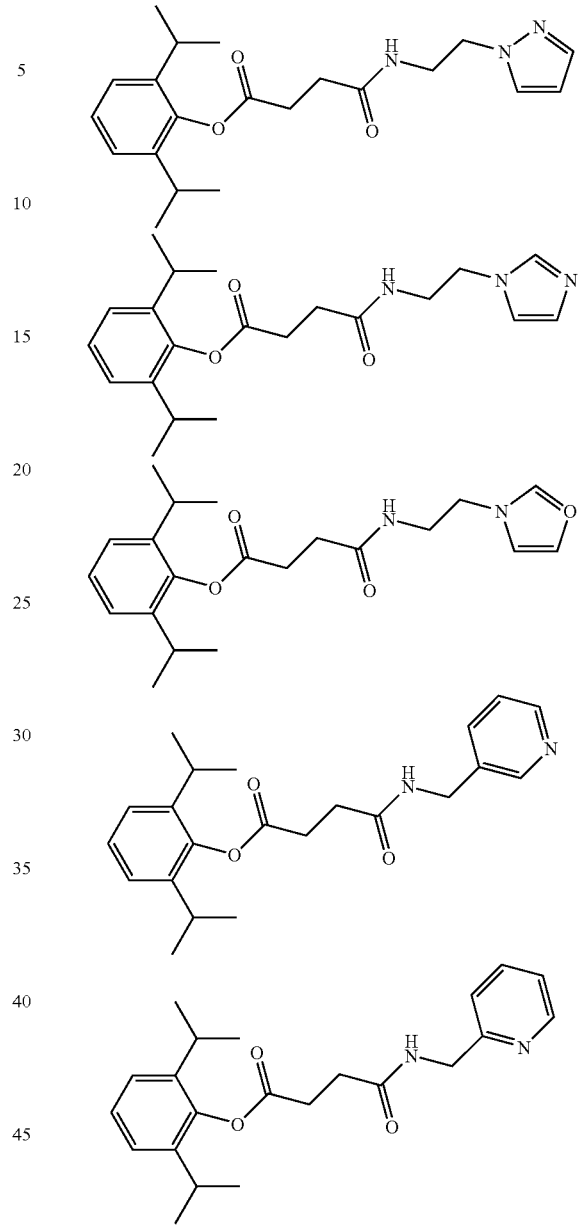

Before the present compounds, compositions and methods are disclosed and described, it is to be understood that this invention is not limited to specific synthetic methods, specific pharmaceutical carriers, or to particular pharmaceutical formulations or administration regimens, as such may, of course, vary. It is also to be understood that the terminology used herein is for the purpose of describing particular aspects only and is not intended to be limiting.

It must be noted that, as used in the specification and the appended claims, the singular forms "a," "an" and "the" include plural referents unless the context clearly dictates otherwise. Thus, for example, reference to "a bicyclic aromatic compound" includes mixtures of bicyclic aromatic compounds, reference to "a pharmaceutical carrier" includes mixtures of two or more such carriers, and the like.

Certain pharmaceutically acceptable salts of the invention are prepared by treating the novel compounds of the invention with an appropriate amount of pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to about 100° C., preferably at room temperature. The molar ratio of compounds of structural formula A to base used is chosen to provide the ratio desired for any particular salts. For preparing, for example, the ammonium salts of the starting material, compounds of formula A can be treated with approximately one equivalent of the pharmaceutically acceptable base to yield a neutral salt. When calcium salts are prepared, approximately one-half a molar equivalent of base is used to yield a neutral salt, while for aluminum salts, approximately one-third a molar equivalent of base will be used.

2,6-diisopropylphenol and the prodrugs of this invention preferably are delivered as pharmaceutical compositions. "Pharmaceutical composition" refers to a composition suitable for pharmaceutical use in a subject. The pharmaceutical compositions of this invention comprise a pharmacologically effective amount of a compound of the invention and a pharmaceutically acceptable carrier. "Pharmacologically effective amount" refers to that amount of the compound effective to produce the intended pharmacological result, such as for example, inhibit oxidation, induce anesthesia, inhibit vomiting, inhibit convulsions, inhibit itching, or inhibit inflammation. "Pharmaceutically acceptable carrier" refers to any of the standard pharmaceutical carriers, buffers, and excipients, such as a phosphate buffered saline solution, aqueous solutions of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent.

The compounds of the invention can be formulated for administration in a variety of ways. Typical routes of administration include both enteral and parenteral. These include, without limitation, subcutaneous, intramuscular, intravenous, intraperitoneal, intramedullary, intrapericardiac, intrabursal, oral, sublingual, ocular, nasal, topical, transdermal, transmucosal, or anal. The mode of administration can be, such as for example, via swallowing, inhalation, injection or topical application to a surface (such as for example, eyes, mucus membrane, skin).

Particular formulations typically are appropriate for specific modes of administration. Various contemplated formulations include, for example, aqueous solutions, solid formulations, aerosol formulations and transdermal formulations.

Examples of aqueous solutions include, for example, water, saline, phosphate buffered saline, Hank's solution, Ringer's solution, dextrose/saline, glucose solutions and the like. The compositions can contain pharmaceutically acceptable auxiliary substances as required to approximate physiological conditions or to improve stability, appearance or ease of administration, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

Aqueous solutions are appropriate for injection and, in particular, for intravenous injection. Intravenous injection is a particularly appropriate means of delivery for using the compound as a hypnotic agent. The intravenous solution can include detergents and emulsifiers such as lipids. Aqueous solutions also are useful for enteral administration as tonics and administration to mucous or other membranes as, such as for example, nose or eye drops. The composition can contain the compound in an amount of about 1 milligram per milliliter to 100 milligram per milliliter, more preferably about 10 milligram per milliliter.

Solid compositions are appropriate for enteral administration. They can be formulated in the form of, such as for example, pills, tablets, powders or capsules. For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10%-95% of active ingredient.

The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, maltose, rice, flour, chalk, silica gel, magnesium stearate, sodium stearate, glycerol monostearate, sodium chloride, dried skim milk, glycerol, propylene glycol, water, ethanol, and the like.

A unit dosage form, such as a tablet, can have about 10 milligram to about 2 gram of the compound.

Solid compositions are particularly useful for using the compound as an anti-emetic. Systemic administration can also be by transmucosal or transdermal means.

For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents can be used to facilitate permeation. Transmucosal administration can be through nasal sprays, for example, or using suppositories.

For topical administration, the agents are formulated into ointments, creams, salves, powders and gels. In one aspect, the transdermal delivery agent can be DMSO.

Transdermal delivery systems can include, such as for example, patches.

Topical administration is particularly useful for use of the compound as an anti-pruritic or in the treatment of wounds with an inflammatory component such as burns, rashes and sunburns. However, sustained administration can deliver the compound for use as an anti-oxidant and anti-inflammatory agent internally.

For inhalation, the compound is preferably administered in the form of an aerosol, liquid or solid. For aerosol administration, the compound preferably is supplied in finely divided form along with a surfactant and propellant. A surfactant may be required if the agent is immiscible in the propellant.

The surfactant preferably is soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides, can be employed. The surfactant can constitute 0.1%-20% by weight of the composition, preferably 0.25%-5%.

The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the agent as a solution or as finely divided particles and surfactant. The ingredients are thus maintained at an elevated pressure until released by action of the valve.

A nebulizer or aerosolizer device for administering compounds typically delivers a dose of about concentration of between about 1 and 50 milligram per inhalation.

Delivery by inhalation is particularly effective for delivery to respiratory tissues for the treatment of respiratory conditions including an inflammatory component. Delivery of large doses by respiration also can induce sedation or anaesthesia. Anesthesia may be achieved by means of continuous inhalation such as occurs with 2,6-diisopropylphenol, ether, or other conventional anesthetics. Induction may occur at doses between about 200 milligram and about 400 milligram inhaled over a period of a few minutes (such as for example, about 5 to about 15 minutes). Sedation may be maintained thereafter at a dose of about 200 milligram to about 400 milligram per hour for as long as is needed.

In preparing pharmaceutical compositions of the present invention, it can be desirable to modify the complexes of the present invention to alter their pharmacokinetics and biodistribution. For a general discussion of pharmacokinetics, See, Remington's Phamaceutical Sciences, supra, Chapters 37-39. A number of methods for altering pharmacokinetics and biodistribution are known to one of ordinary skill in the art. Examples of such methods include protection of the complexes in vesicles composed of substances such as proteins, lipids (for example, liposomes), carbohydrates, or synthetic polymers.

Single or multiple administrations of the compositions can be carried out with dose levels and pattern being selected by the treating physician. In any event, the pharmaceutical formulations should provide a quantity of a compound sufficient to treat the patient effectively.

The total effective amount of a compound of the present invention can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a compound of the present invention required to obtain an effective dose in a subject depends on many factors including the age and general health of the subject, the route of administration, the number of treatments to be administered and the judgement of the prescribing physician. In view of these factors, the skilled artisan would adjust the dose so as to provide an effective dose for a particular use.

EXAMPLES

Used herein, the following abbreviations have the following meanings: Me refers to methyl ($CH_3$—), Et refers to ethyl ($CH_3CH_2$—), i-Pr refers to isopropyl ($(CH_3)_2CH_2$—), t-Bu or tert-butyl refers to tertiary butyl ($(CH_3)_3CH$—), Ph refers to phenyl, Bn refers to benzyl ($PhCH_2$—), Bz refers to benzoyl (PhCO—), MOM refers to methoxymethyl, Ac refers to acetyl, TMS refers to trimethylsilyl, TBS refers to ter-butyldimethylsilyl, Ms refers to methanesulfonyl ($CH_3SO_2$—), Ts refers to p-toluenesulfonyl (p-$CH_3PhSO_2$—), Tf refers to trifluoromethanesulfonyl ($CF_3SO_2$—), TfO refers to trifluoromethanesulfonate ($CF_3SO_3$—), DMF refers to N,N-dimethylformamide, DCM refers to dichloromethane ($CH_2Cl_2$), THF refers to tetrahydrofuran, EtOAc refers to ethyl acetate, $Et_2O$ refers to diethyl ether, MeCN refers to acetonitrile ($CH_3CN$), NMP refers to 1-N-methyl-2-pyrrolidinone, DMA refers to N,N-dimethylacetamide, DMSO refers to dimethylsulfoxide, DCC refers to 1,3-dicyclohexyldicarbodiimide, EDCl refers to 1-(3-dimethylaminopropyl)-3-ethylcarbodiimide, Boc refers to tert-butylcarbonyl, Fmoc refers to 9-fluorenylmethoxycarbonyl, TBAF refers to tetrabutylammonium fluoride, TBAI refers to tetrabutylammonium iodide, TMEDA refers to N,N,N,N-tetramethylethylene diamine, Dess-Martin periodinane or Dess Martin reagent refers to 1,1,1-triacetoxy-1,1-dihydro-1,2-benziodoxol-3 (1H)-one, DMAP refers to 4-N,N-dimethylaminopyridine, (i-Pr)$_2$NEt or DIEA or Hunig's base refers to N,N-diethylisopropylamine, DBU refers to 1,8-Diazabicyclo[5.4.0]undec-7-ene, (DHQ)$_2$AQN refers to dihydroquinine anthraquinone-1,4-diyl diether, (DHQ)$_2$PHAL refers to dihydroquinine phthalazine-1,4-diyl diether, (DHQ)$_2$PYR refers to dihydroquinine 2,5-diphenyl-4,6-pyrimidinediyl diether, (DHQD)$_2$AQN refers to dihydroquinidine anthraquinone-1,4-diyl diether, (DHQD)$_2$PHAL refers to dihydroquinidine phthalazine-1,4-diyl diether, (DHQD)$_2$PYR refers to dihydroquinidine 2,5-diphenyl-4,6-pyrimidinediyl diether, LDA refers to lithium diisopropylamide, LiTMP refers to lithium 2,2,6,6-tetramethylpiperdinamide, n-BuLi refers to n-butyllithium, t-BuLi refers to tert-butyl lithium, IBA refers to 1-hydroxy-1,2-benziodoxol-3 (1H)-one 1-oxide, $OsO_4$ refers to osmium tetroxide, m-CPBA refers to meta-chloroperbenzoic acid, DMD refers to dimethyl dioxirane, PDC refers to pyridinium dichromate, NMO refers to N-methyl morpholine-N-oxide, NaHMDS refers to sodium hexamethyldisilazide, LiHMDS refers to lithium hexamethyldisilazide, HMPA refers to hexamethylphosphoramide, TMSCl refers to trimethylsilyl chloride, TMSCN refers to trimethylsilyl cyanide, TBSCl refers to tert-butyldimethylsilyl chloride, TFA refers to trifluoroacetic acid, TFAA refers to trifluoroacetic anhydride, AcOH refers to acetic acid, $Ac_2O$ refers to acetic anhydride, AcCl refers to acetyl chloride, TsOH refers to p-toluenesulfonic acid, TsCI refers to p-toluenesulfonyl chloride, MBHA refers to 4-methylbenzhydrylamine, BHA refers to benzhydrylamine, $ZnCl_2$ refers to zinc (II) dichloride, $BF_3$ refers to boron trifluoride, Y $(OTf)_2$ refers to yttrium (III) trifluoromethanesulfonate, Cu $(BF_4)_2$ refers to copper (II) tetrafluoroborate, LAH refers to lithium aluminum hydride (LiAlH₄), NaHCO₃ refers to sodium bicarbonate, K₂CO₃ refers to potassium carbonate, NaOH refers to sodium hydroxide, KOH refers to potassium hydroxide, LiOH refers to lithium hydroxide, HCl refers to hydrochloric acid, H₂SO₄ refers to sulfuric acid, MgSO₄ refers to magnesium sulfate, and Na₂SO₄ refers to sodium sulfate. $^1$H NMR refers to proton nuclear magnetic resonance, $^{13}$C NMR refers to carbon 13 nuclear magnetic resonance, NOE refers to nuclear overhauser effect, NOESY refers to nuclear overhauser and exchange spectroscopy, COSY refers to homonuclear correlation spectroscopy, HMQC refers to proton detected heteronuclear multiplet-quantum coherence, HMBC refers to heteronuclear multiple-bond connectivity, s refers to singlet, br s refers to broad singlet, d refers to doublet, br d refers to broad doublet, t refers to triplet, q refers to quartet, dd refers to double doublet, m refers to multiplet, ppm refers to parts per million, IR refers to infrared spectrometry, MS refers to mass spectrometry, HRMS refers to high resolution mass spectrometry, EI refers to electron impact, FAB refers to fast atom bombardment, CI refers to chemical ionization, HPLC refers to high pressure liquid chromatography, TLC refer to thin layer chromatography, $R_f$ refers to, $R_t$ refers to retention time, GC refers to gas chromatography, min is minutes, h is hours, rt or RT is room temperature, gram is grams, mg is milligrams, L is liters, mL is milliliters, mol is moles and mmol is millimoles.

For all of the following examples, standard work-up and purification methods can be utilized and will be obvious to those skilled in the art. Synthetic methodologies that make up the invention are shown in Schemes 1-3. These Schemes are intended to describe the applicable chemistry through the use of specific examples and are not indicative of the scope of the invention.

Example 1

Propofol Hemisuccinate

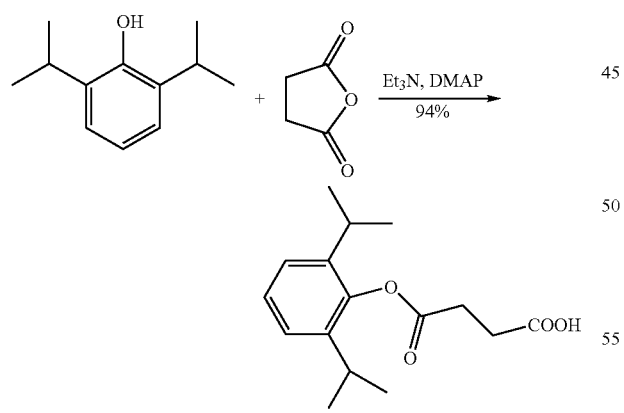

To a solution of 2,6-diisopropylphenol (4.0 g, 22.4 mmol) in 15 mL of Et₃N was added succinic anhydride (2.8 g, 28 mmol) and a catalytic amount of DMAP (10 mg) under N₂ atmosphere. The reaction mixture was stirred at ambient temperature overnight. The solvent was removed under vacuum and the residue was dissolved in water (30 mL) and added to a cold solution of 1 N HCl (150 mL). The precipitate was filtered and dried. Recrystallization from ethanol-water (2:1) mixture gave 2,6-diisopropylphenyl hemisuccinate as a white crystalline solid. Yield: 5.8 gram (94%).

$^1$H-NMR (CDCl₃) δ ppm: 1.2 (d, 12H), 2.82-2.84 (m, 2H), 2.85-3.0 (m, 4H), 7.1-7.21 (m, 3H).

Example 2

N-(2-Pyrrolidin-1-yl-ethyl)-succinamic acid 2,6-diisopropylphenyl ester

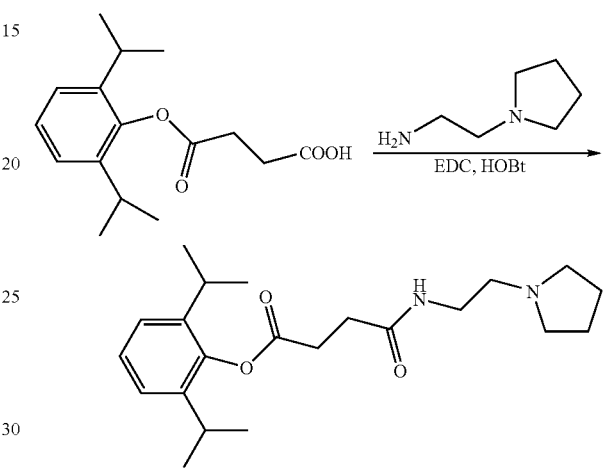

To a solution of propofol hemisuccinate (2.0 g, 7.2 mmol) in THF—CH₂Cl₂ (1:1, 60 mL) was added EDCl (1.72 g, 9 mmol) followed by HOBt (1.37 g, 9 mmol). The reaction mixture was stirred at ambient temperature for 15 min and 1-(2-aminoethyl)pyrrolidine (0.912 g, 8 mmol) was added and stirring was maintained overnight. 10% aqueous citric acid (50 ml) was added and the mixture was extracted with CH₂Cl₂ (100 ml×2). The organic layer was washed with brine and dried over anhydrous MgSO₄. The solvent was removed and the product was purified by silica gel column chromatography using acetone with 1% Et₃N. Removal of the solvent gave the product as an oil. Yield: 2.47 gram (92%)

$^1$H-NMR (CDCl₃) δ ppm: 1.2 (d, 12H), 1.8 (m, 4H), 2.2 (d, 1H), 2.6 (m, 8H), 2.95 (m, 4H), 3.36 (m, 2H), 7.2 (m, 3H).

Example 3

N-(2-Piperidin-1-yl-ethyl)-succinamic acid 2,6-diisopropylphenyl ester

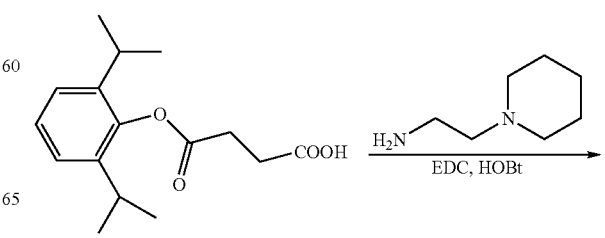

-continued

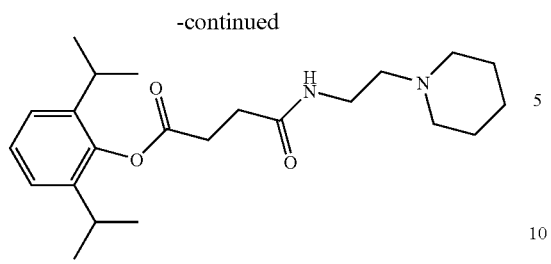

Prepared according to example 2. Yield: 86%
$^1$H-NMR (CDCl$_3$) δ ppm: 1.2 (d, 12H), 1.44 (m, 2H), 1.6 (m, 4H), 2.42 (t, 5H), 2.6 (t, 2H), 2.90 (m, 4H), 3.32 (m, 4H), 7.18 (m, 3H).

Example 4

N-(2-Dimethylaminoethyl)-succinamic acid 2,6-diisopropyl-phenyl ester

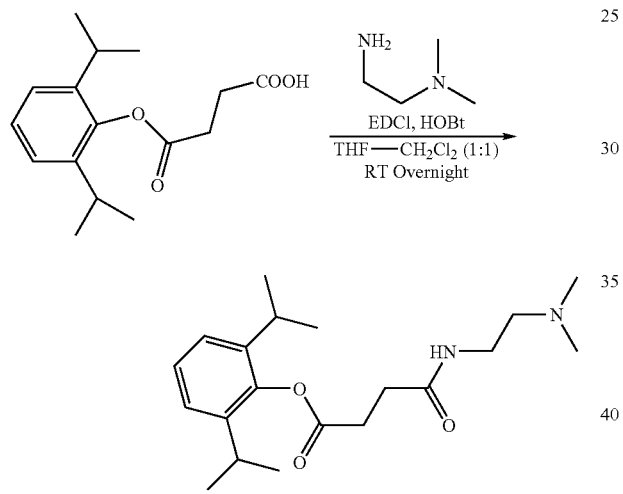

Prepared according to example 2. Yield: 64%—Rf: 0.55 (in 50% MeOH—CH$_2$Cl$_2$)
$^1$H NMR (300 MHz, CD$_3$OD) δ ppm: 1.2 (d, 12H), 2.3 (s, 6H), 2.45 (t, 2H), 2.6 (t, 2H), 3.0 (m, 3H), 3.36 (m, 3H), 7.2 (m, 3H)

Example 5

N-(2-Diethylaminoethyl)-succinamic acid 2,6-diisopropylphenyl ester

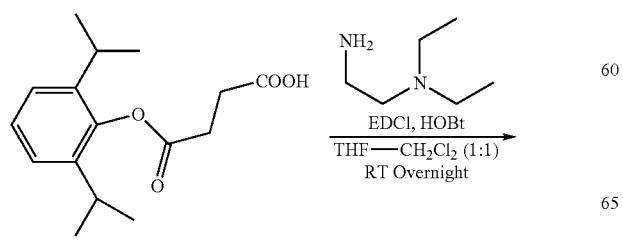

-continued

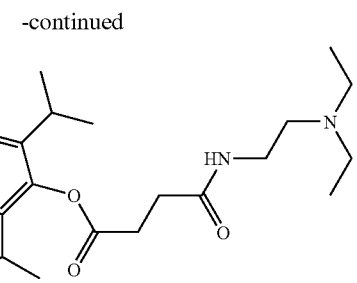

Prepared according to example 2. Yield: 50%; Rf: 0.6 (in 20% MeOH-CH$_2$Cl$_2$)
$^1$H NMR (300 MHz, CDCl$_3$) δ ppm: 1 (t, 6H), 1.2 (d, 12H), 2.57 (m, 6H), 2.62 (t, 2H), 2.9 (m, 2H), 3.2 (t, 2H), 3.3 (m, 2H), 6.2 (br s, 1H), 7.2 (s, 3H)

Example 6

N-(2-Diisopropylaminoethyl)-succinamic acid 2,6-diisopropyl-phenyl ester

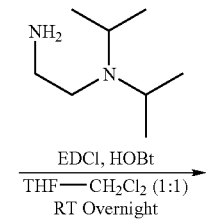

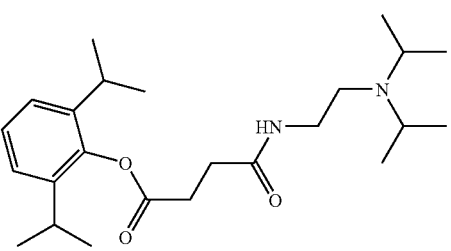

Prepared according to example 2. Yield: 99%; Rf: 0.5 (in 20% MeOH-CH$_2$Cl$_2$+1% Et$_3$N)
$^1$H NMR (300 MHz, CDCl$_3$) δ ppm: 1.0 (d, 12H), 1.2 (d, 12H), 2.6 (m, 4H), 2.9 (m, 2H), 3.1 (m, 4H), 3.35 (m br, 2H) 7.2 (s, 3H)

Example 7

N-(2-Morpholin-4-yl-ethyl)-succinamic acid 2,6-diisopropylphenyl ester

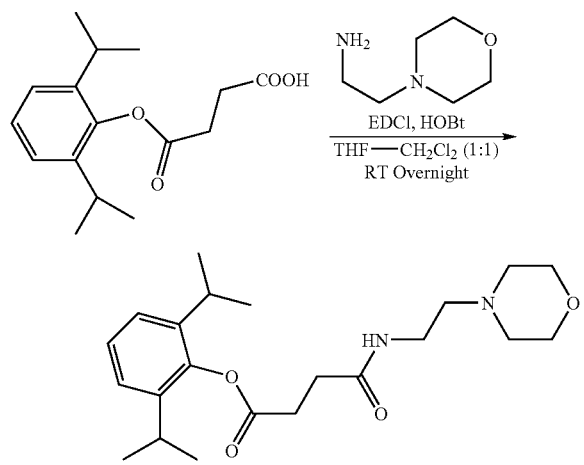

Prepared according to example 2. Yield: 68%; Rf: 0.8 (20% MeOH-CH$_2$Cl$_2$+1% Et$_3$N)

$^1$H NMR (300 MHz, CDCl$_3$) δ ppm: 1.2 (d, 12H), 2.45 (m, 6H), 2.6 (t, 2H), 2.9 (m, 2H), 3.12 (t, 2H), 3.35 (m, 2H), 3.7 (m, 4H), 6.15 (t br, 1H), 7.2 (m, 3H)

Example 8

N-(2-Pyrrolidin-1-yl-ethyl)-succinamic acid 2,6-diisopropylphenyl ester hydrochloride

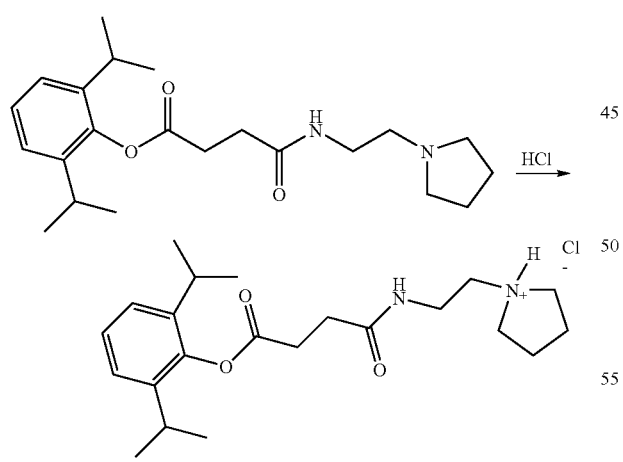

A solution of N-(2-Pyrrolidin-1-yl-ethyl)-succinamic acid 2,6-diisopropylphenyl ester (700 mg) in 100 ml of ether was cooled to 0° C. and dry HCl gas was bubbled in for 10 min. The precipitate was filtered, washed with ether and dried under high vacuum to yield N-(2-Pyrrolidin-1-yl-ethyl)-succinamic acid 2,6-diisopropylphenyl ester hydrochloride as a white crystalline solid. Yield: 590 mg (77%).

$^1$H-NMR (D$_2$O) δ ppm: 1.05 (d, 12H), 1.85 (m, 2H), 2.05 (m, 2H), 2.6 (m, 2H), 2.8 (m, 2H), 2.95 (m, 4H), 3.2 (m, 2H), 3.45 (m, 2H), 3.55 (m, 2H), 7.2 (m, 3H).

Example 9

N-(2-Piperidin-1-yl-ethyl)-succinamic acid 2,6-diisopropylphenyl ester hydrochloride

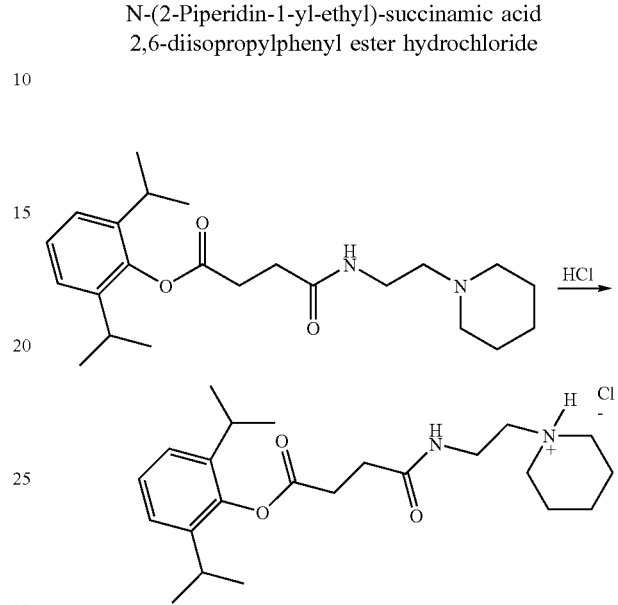

Yield: 584 mg (86%).

$^1$H-NMR (D$_2$O) δ ppm: 1.05 (d, 12H), 1.3 (m, 1H), 1.6 (m, 3H), 1.8 (m, 2H), 2.6 (m, 2H), 2.8 (m, 4H), 2.95 (m, 2H), 3.1 (m, 2H), 3.4 (m, 2H), 3.5 (m, 2H), 7.2 (m, 3H).

Example 10

N-(2-Dimethylamino-ethyl)-succinamic acid 2,6-diisopropyl-phenyl ester Hydrochloride

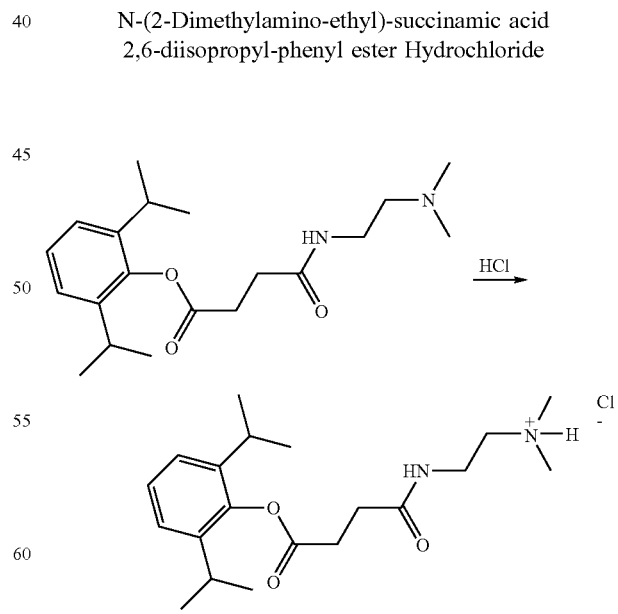

Prepared according to example 8. Yield: 49%

$^1$H-NMR (D$_2$O) δ ppm: 0.98 (d, 12H), 2.57 (t, 2H), 2.75 (m, 8H), 2.9 (t, 2H), 3.1 (t, 2H), 3.45 (t, 2H), 7.15 (m, 3H)

Example 11

N-(2-Diethylamino-ethyl)-succinamic acid 2,6-diisopropyl-phenyl ester Hydrochloride

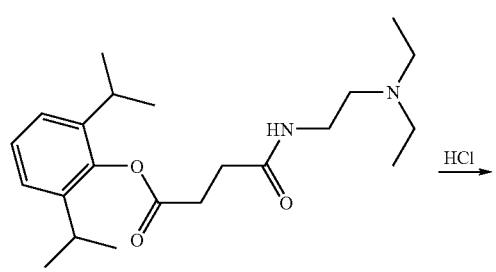

Prepared according to example 8. Yield: 49%

¹H-NMR (D$_2$O) δ ppm: 0.98 (d, 12H), 1.11 (t, 6H), 2.57 (t, 2H), 2.75 (m, 2H), 2.79 (t, 2H), 3.1 (m, 6H), 3.45 (t, 2H), 7.15 (m, 3H), 7.45 (s, 1H).

Example 12

N-(2-Diisopropylamino-ethyl)-succinamic acid 2,6-diisopropyl-phenyl ester Hydrochloride

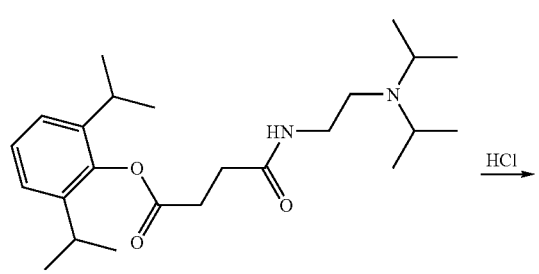

Prepared according to example 8. Yield: 99%

¹H-NMR (D$_2$O) δ ppm: 0.98 (d, 12H), 1.17 (d, 12H), 2.59 (t, 2H), 2.75 (m, 2H), 2.9 (t, 2H), 3.1 (t, 2H), 3.38 (t, 2H), 3.6 (m, 2H), 7.15 (m, 3H), 7.45 (s, 1H).

Example 13

N-(2-Morpholin-4-yl-ethyl)-succinamic acid 2,6-diisopropylphenyl ester Hydrochloride

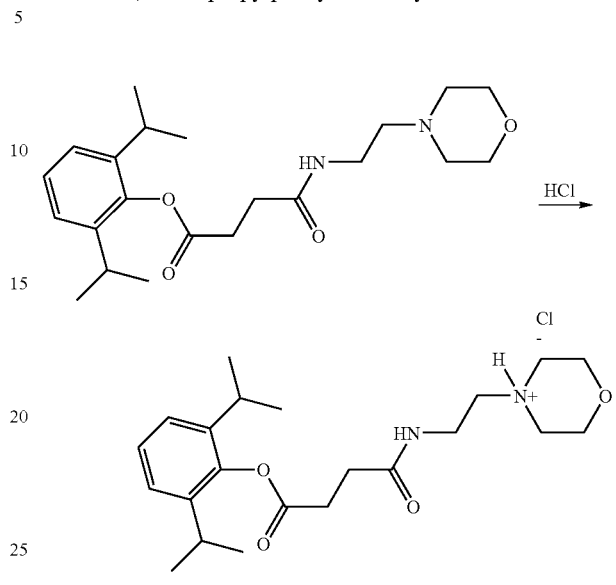

Prepared according to example 8. Yield: 69%

¹H-NMR (D$_2$O) δ ppm: 0.98 (d, 12H), 2.59 (t, 2H), 2.75 (m, 2H), 2.9 (t, 2H), 3.04 (m br, 2H), 3.17 (t, 2H), 3.38 (m br, 2H), 3.48 (t, 2H), 3.61 (m br, 2H), 3.89 (m br, 2H), 7.15 (m, 3H).

Example 14

N-(2-Dibutylaminoethyl)-succinamic acid 2,6-diisopropyl-phenyl ester

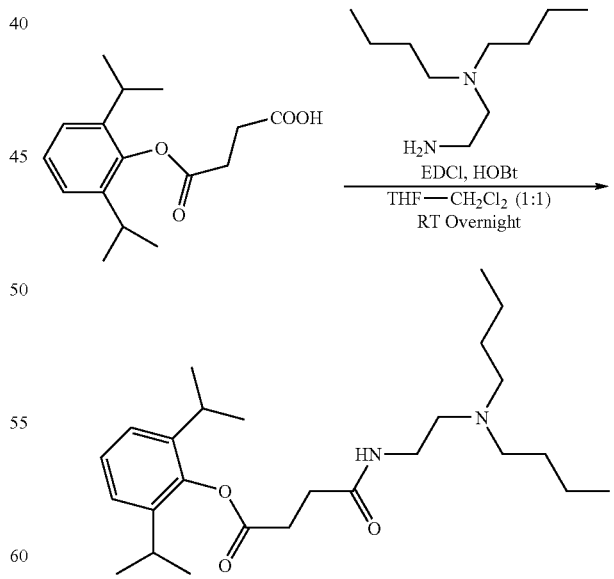

Prepared according to example 2. Yield: 94%; Rf: 0.55 (in 5% MeOH-DCM)

¹H NMR (300 MHz, CDCl$_3$) δ ppm: 0.95 (t, 6H), 1.2 (d, 12H), 1.22-1.42 (m, 8H), 2.4 (t, 4H), 2.45-2.6 (m, 4H), 2.9 (m, 2H), 3.02 (t, 2H), 3.3 (m, 2H), 7.1 (m, 3H)

Example 15

N-(2-Dibutylaminoethyl)-succinamic acid 2,6-diisopropyl-phenyl ester hydrochloride

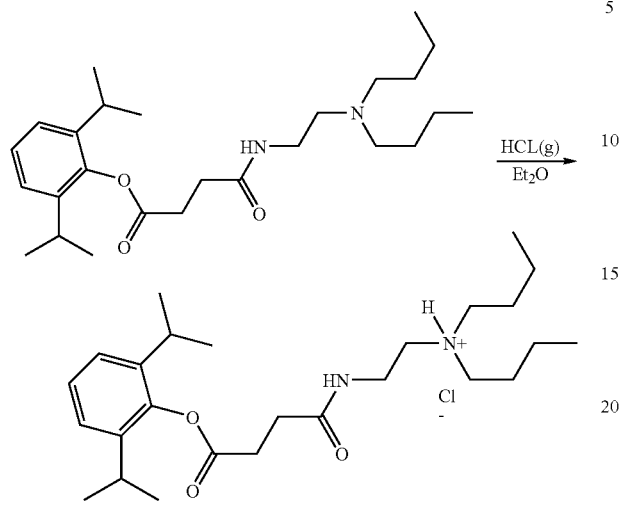

Prepared according to example 8. Yield: 92%.

$^1$H NMR (300 MHz, D$_2$O) δ ppm: 0.77 (t, 6H), 0.99 (d, 12H), 1.18 (m, 4H), 1.48 (m, 4H) 2.58 (m, 2H), 2.75 (m, 2H), 2.9 (m, 2H), 3.0 (m, 4H), 3.12 (m, 2H), 3.42 (m, 2H), 7.1 (m, 3H)

Example 16

In-vitro hydrolysis of N-(2-piperidin-1-yl-ethyl)-succinamic acid 2,6-diisopropylphenyl ester hydrochloride A solution was prepared by dissolving 5 mg of N-(2-Piperidin-1-yl-ethyl)-succinamic acid 2,6-diisopropylphenyl ester hydrochloride in 12 mL of pH=7.4 phosphate buffer. The solution was incubated at 37° C. and aliquots were drawn at 5, 15, 30 and 45 minutes and analyzed by reverse phase HPLC. A plot of UV absorption versus time clearly demonstrates the hydrolysis of the prodrug at pH=7.4.

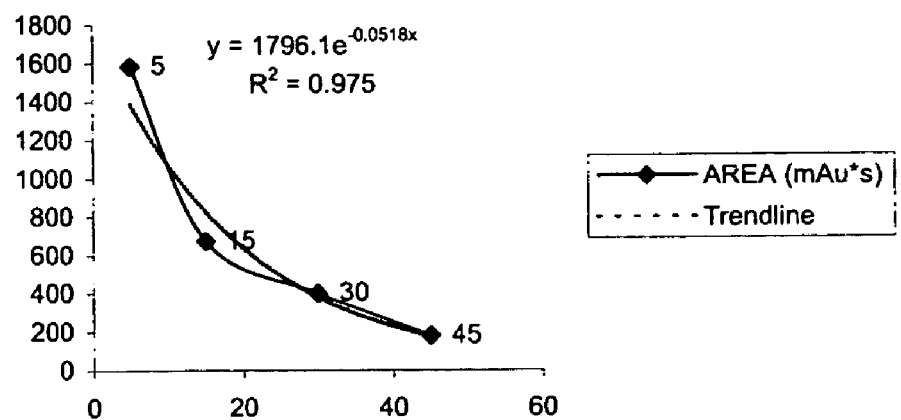

Example 17 pH Stability of
N-(2-piperidin-1-yl-ethyl)-succinamic acid
2,6-diisopropylphenyl ester hydrochloride A solution was prepared by dissolving 100 mg of N-(2-Piperidin-1-yl-ethyl)-succinamic acid 2,6-diisopropylphenyl ester hydrochloride in 10 mL of pH=4.1 sodium acetate buffer. The buffer was prepared by adding NaOH to a 20% aqueous acetic acid solution until the desired pH was reached. The solution was incubated at ambient temperature and analyzed by LC-MS after 48 hours. No trace of decomposition was observed.

Example 18

In-vivo Induction of Anesthesia

Prodrugs were formulated as aqueous isotonic solutions at pH 7.4 in sterile water before administration to animals. Female mice were obtained from Charles River Laboratories (Wilmington, Mass.). The volume of injection was set at 10 mg/kg/animal and animals were dosed IP at 100 mg/kg, 125 mg/kg, 150 mg/kg and 200 mg/kg. The monitoring of distinguishable levels of sedation started immediately after an injection and was continued for a 2-h period post-injection. The sedation level was graded according to the behavioral and reflex activity of animals injected with progressively increasing doses of each compound. Animals were graded as alert and normal when there was no observable change in their behavior; alert with decreased motor activity when ataxia with some ability to walk was observed; and awake and recumbent when loss of righting reflex occurred. Animals reaching somnolence but retaining response to painful stimuli (toe or tail pinch) were graded as sedated with normal reflexes, whereas animals that lost response to painful stimuli were graded as sedated with decreased reflexes (anesthetic level of sedation). Death resulting from the overdose was also recorded as a last level.

N-(2-Pyrrolidin-1-yl-ethyl)-succinamic acid
2,6-diisopropylphenyl ester hydrochloride 150 mg/kg: Onset of sedation—2 minutes post injection; Full anesthesia—4 minutes post injection; Duration of anesthesia—10 minutes (14 minutes post injection).
200 mg/kg: Onset of sedation—2 minutes post injection; Full anesthesia—4 minutes post injection; Duration of anesthesia—21 minutes (25 minutes post injection).

N-(2-Piperidin-1-yl-ethyl)-succinamic acid
2,6-diisopropylphenyl ester hydrochloride 100 mg/kg: Onset of sedation—2 minutes post injection; Full anesthesia—not reached; Duration of anesthesia—11 minutes (13 minutes post injection).
125 mg/kg: Onset of sedation—2 minutes post injection; Full anesthesia—not reached; Duration of sedation—13 minutes (15 minutes post injection).
200 mg/kg: Onset of sedation—2 minutes post injection; Full anesthesia—5 minutes post injection; Duration of anesthesia—12 minutes (16 minutes post injection).

The present invention provides pH sensitive, water soluble derivatives of 2,6-diisopropylphenol and methods of using these compounds. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

What is claimed is:

1. A compound of formula A:

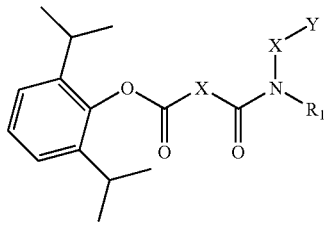

Formula A wherein:

$R_1$ is hydrogen, alkyl, or aryl;

Each X is independently $C_{1-10}$ alkyl;

Y is heteroaryl, saturated heterocyclic, or $NR_2R_3$, $R_2$ and $R_3$ are independently hydrogen, alkyl, or $R_2$ and $R_3$, together with the nitrogen atom to which they are attached, combine to form a saturated heterocyclic or heteroaryl ring;

or pharmaceutically acceptable salts of any of the foregoing.

2. A pharmaceutical composition comprising a pharmaceutically acceptable carrier and a pharmacologically effective amount of a compound according to claim 1.

3. A pharmaceutical composition of claim 2, wherein the pharmaceutically acceptable carrier is selected from an aqueous solution, an injectable solution, an aeorsolizer, an inhaler or a transdermal delivery vehicle.

4. A pharmaceutical composition of claim 2 contained in a unit dosage form.

5. The pharmaceutical composition of claim 2 wherein the pharmaceutically acceptable carrier comprises a transdermal delivery vehicle, wherein the pharmaceutically acceptable carrier contains a detergent, an emulsifier or liposomes.

6. The pharmaceutical composition of claim 2 in the form of an injectable solution wherein the concentration of the compound in the injectable solution is between about 0.5 milligram per milliliter to about 200 milligram per milliliter.

7. The pharmaceutical composition of claim 2 contained in a unit dosage form wherein the unit dosage form contains about 0.5 milligram to about 1.2 gram of the compound.

8. A method for inducing anesthesia, the method comprising administering to a subject in need thereof an effective amount of at least one compound according to claim 1, wherein the compound according to claim 1 is administered in the form of an intravenous injection of an aqueous composition comprising the compound.

9. A compound selected from:
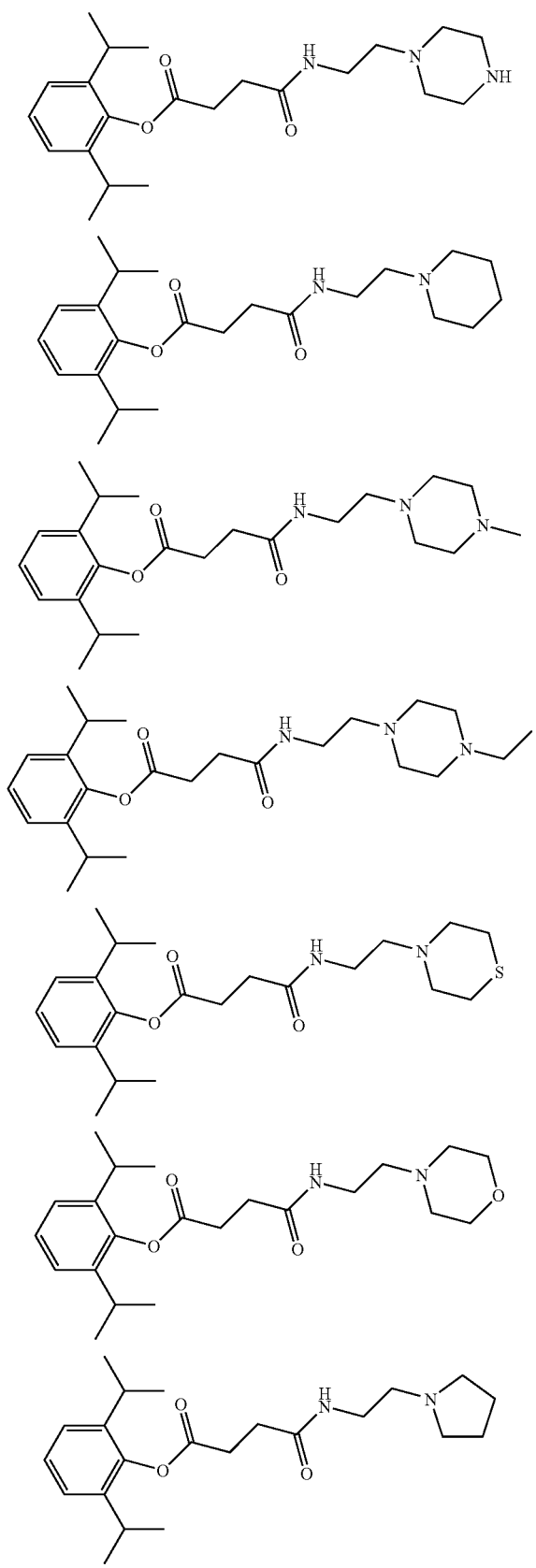
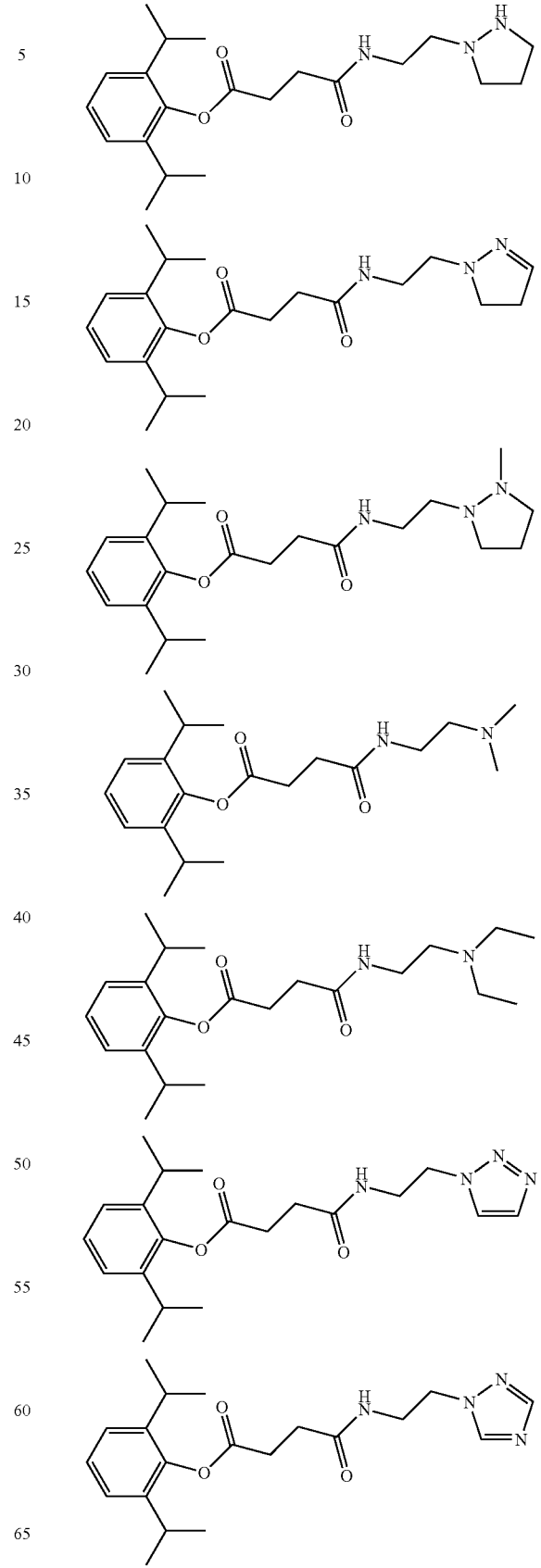

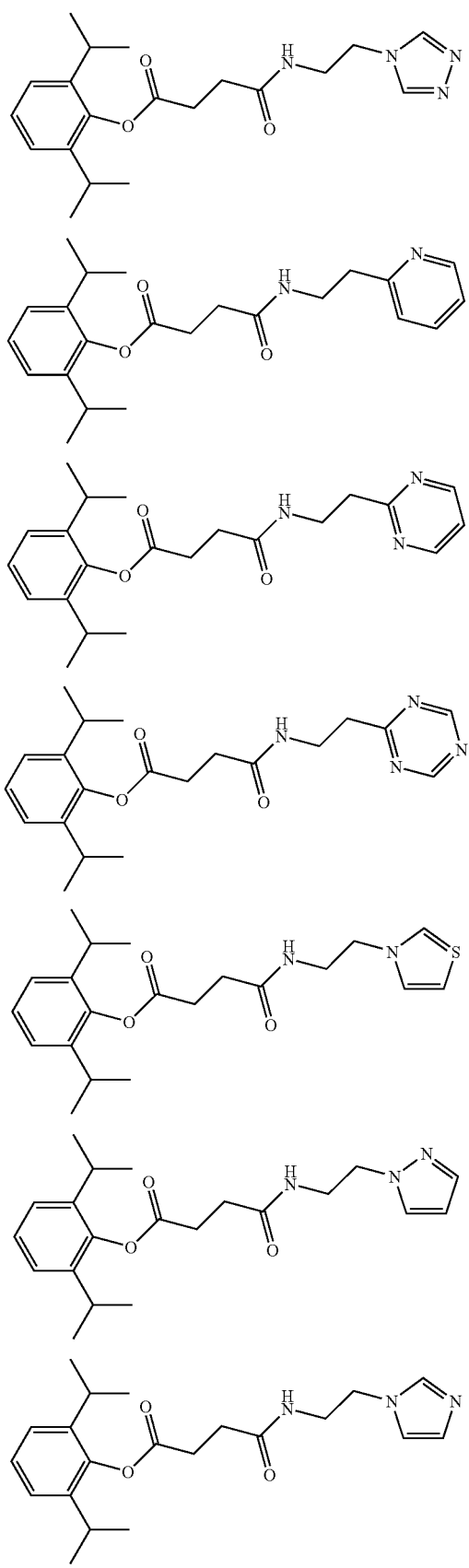
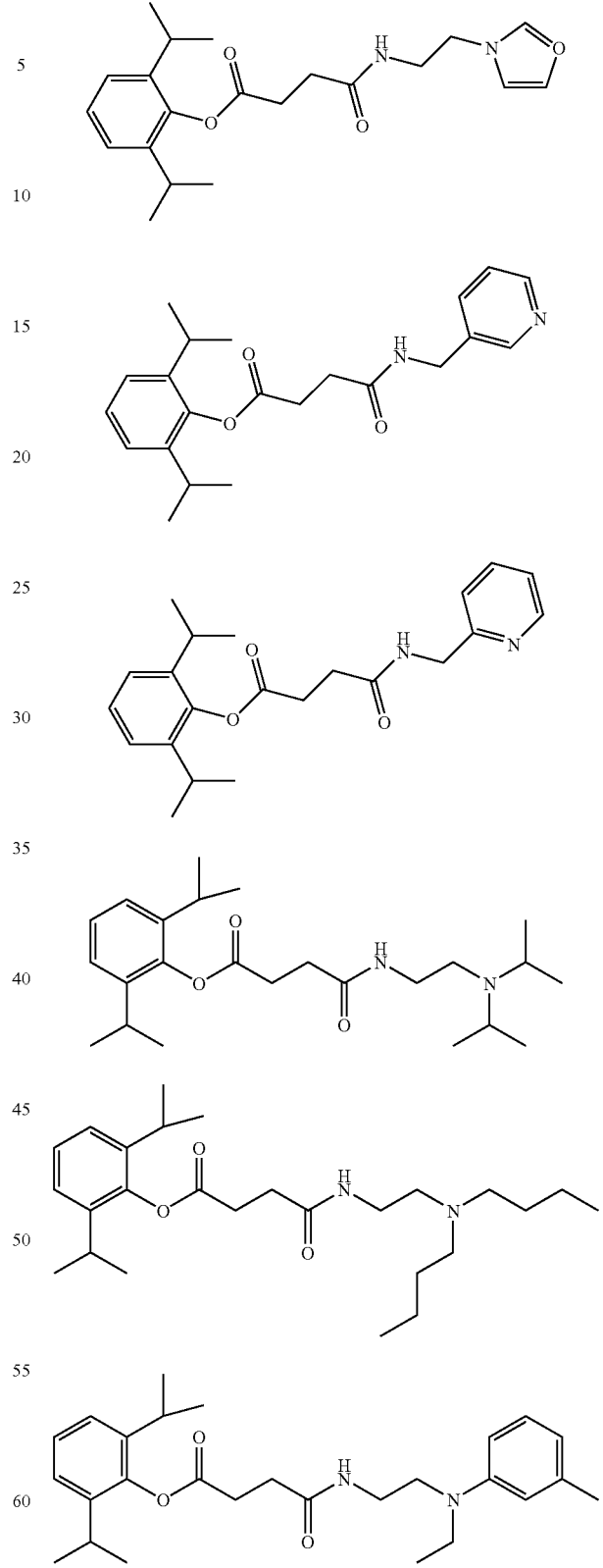
and pharmaceutically acceptable salts of any of the foregoing.
* * * * *